US010712350B2

(12) United States Patent
Kiehntopf et al.

(10) Patent No.: US 10,712,350 B2
(45) Date of Patent: Jul. 14, 2020

(54) DIAGNOSIS OF SEPSIS AND SYSTEMIC INFLAMMATORY RESPONSE SYNDROME

(71) Applicant: UNIVERSITÄTSKLINIKUM JENA, Jena (DE)

(72) Inventors: Michael Kiehntopf, Jena (DE); Diana Schmerler, Jena (DE); Thomas Deufel, Jena (DE); Frank Brunkhorst, Jena (DE)

(73) Assignee: UNIVERSITÄTSKLINIKUM, JENA, Jena (DE)

(*) Notice: Subject to any disclaimer, the term of this patent is extended or adjusted under 35 U.S.C. 154(b) by 568 days.

(21) Appl. No.: 15/373,872

(22) Filed: Dec. 9, 2016

(65) Prior Publication Data
US 2017/0242035 A1 Aug. 24, 2017

Related U.S. Application Data

(63) Continuation of application No. 13/261,860, filed as application No. PCT/EP2012/072644 on Nov. 14, 2012, now abandoned.

(30) Foreign Application Priority Data

Nov. 14, 2011 (EP) .................................... 11189024

(51) Int. Cl.
G01N 33/53 (2006.01)
G01N 33/68 (2006.01)
C07K 14/81 (2006.01)
G06F 19/00 (2018.01)
G16H 50/30 (2018.01)
C07K 16/38 (2006.01)

(52) U.S. Cl.
CPC ..... *G01N 33/6893* (2013.01); *C07K 14/8125* (2013.01); *C07K 16/38* (2013.01); *G01N 33/5308* (2013.01); *G01N 33/6848* (2013.01); *G06F 19/00* (2013.01); *G16H 50/30* (2018.01); *C07K 2317/34* (2013.01); *G01N 2333/8125* (2013.01); *G01N 2570/00* (2013.01); *G01N 2800/26* (2013.01); *G01N 2800/52* (2013.01); *G01N 2800/56* (2013.01)

(58) Field of Classification Search
None
See application file for complete search history.

(56) References Cited

U.S. PATENT DOCUMENTS

| 4,711,848 | A | 12/1987 | Insley et al. |
| 5,114,863 | A | 5/1992 | McCombs et al. |
| 8,506,957 | B2 | 8/2013 | Leeds et al. |
| 2006/0029956 | A1 | 2/2006 | Beyer et al. |
| 2009/0075266 | A1 | 3/2009 | Shuber |
| 2009/0104605 | A1 | 4/2009 | Siuzdak et al. |
| 2014/0248631 | A1 | 9/2014 | Kiehntopf et al. |

FOREIGN PATENT DOCUMENTS

| CN | 1777682 | A | 5/2006 |
| CN | 101014862 | A | 8/2007 |
| CN | 101622360 | A | 1/2010 |
| CN | 101661032 | A | 3/2010 |
| CN | 102153628 | A | 8/2011 |
| CN | 201280067006 | | 11/2012 |
| DE | 102005056839 | A1 | 6/2007 |
| EP | 2060920 | A1 | 5/2009 |
| EP | 11189024 | | 11/2011 |
| EP | 12801471 | | 11/2012 |
| JP | 2014541651 | | 11/2012 |
| WO | WO-99/45940 | A1 | 9/1999 |
| WO | WO-2006/010047 | A2 | 1/2006 |
| WO | WO-2007/022248 | A2 | 2/2007 |
| WO | WO-2007/078841 | A2 | 7/2007 |
| WO | WO-2007/100183 | A1 | 9/2007 |
| WO | WO-2008/031190 | A1 | 3/2008 |
| WO | WO-2010/054195 | A2 | 5/2010 |

(Continued)

OTHER PUBLICATIONS

Van Der Vekiens et al., Human and equine cardiovascular endocrinology: beware to compare, Cardiovascular Endocrinology 2013, vol. 2, No. 4, pp. 67-76. (Year: 2013).*
Torzewski et al., Animal Models of C-Reactive Protein, Hindawl Publishing Corporation, Mediators of Inflammation, vol. 2014, Article ID 683598, 2014, pp. 1-7. (Year: 2014).*
U.S. Appl. No. 13/261,860, filed May 14, 2014, Kiehntopf et al.
Bernstein et al., Transthyretin and the Systemic Inflammatory Response. Current Nutrition & Food Science. 2009; 5(1): 71-4.
Bistrian et al., Acute phase proteins and the systemic inflammatory responses. Crit Care Med. 1999; 27(3): 452.
Bone et al., Definitions for Sepsis and Organ Failure and Guidelines for the Use of Innovative Therapies in Sepsis. The ACCP/SCCM Consensus Conference Committee. American College of Chest Physicians/Society of Critical Care Medicine. Chest. 1992; 101(6):1644-53.

(Continued)

*Primary Examiner* — Gary Counts
(74) *Attorney, Agent, or Firm* — Ballard Spahr LLP

(57) ABSTRACT

The present invention relates a method for the diagnosis, prediction or risk stratification for mortality and/or disease outcome of a subject that has or is suspected to have sepsis, comprising determining the presence and/or level of antitrypsin (ATT) or fragments thereof in a sample taken from said subject and/or determining the presence and/or level of transthyretin (TTR) or fragments thereof, wherein the presence and/or level of ATT and/or TTR or fragments thereof is correlated with an increased risk of mortality and, wherein said increased risk of mortality and/or poor disease outcome is given if the level of ATT is below a certain cut-off value and/or the level of fragments thereof is above a certain cut-off value and/or said increased risk of mortality and/or poor disease outcome is given if the level of TTR is below a certain cut-off value and/or the level of fragments thereof is below a certain cut-off value. The invention relates in general to the use of ATT and/or TTR or its fragments for the diagnosis of sepsis, and to nucleotides of SEQ ID NO. 2 to 14.

7 Claims, 9 Drawing Sheets

Specification includes a Sequence Listing.

(56) References Cited

FOREIGN PATENT DOCUMENTS

| WO | WO-2010/085879 A1 | 8/2010 |
|----|---|---|
| WO | PCT/EP2012/072644 | 11/2012 |
| WO | WO-2013/072381 A1 | 5/2013 |

OTHER PUBLICATIONS

Carrigan et al., Toward Resolving the Challenges of Sepsis Diagnosis. Clinical Chemistry. 2004; 50(8):1301-14.
Devakonda et al., Transthyretin as a Marker to Predict Outcome in Critically Ill Patients. Clin Biochem 41. 2008; 1126-30.
Dichtl et al., The carboxyl-terminal fragment of a1-antitrypsin is present in atherosclerotic plaques and regulates inflammatory transcription factors in primary human monocytes. Mol Cell Biol ResCommun. 2000; 4: 50-61.
Giamarellos-Bourboulis et al., Procalcitonin: A Marker to Clearly Differentiate Systemic Inflammatory Response Syndrome and Sepsis in the Critically Ill Patient? Intensive Care Med. 2002; 28(9):1351-6.
Kiehntopf et al., Mass Spectrometry-Based Protein Patterns in the Diagnosis of Sepsis/Systemic Inflammatory Response Syndrome. Shock. 2011; 36(6):560-9.
Ren et al., The Alterations of Mouse Plasma Proteins During Septic Development. J Proteomo Res. 2007; 6(7):2812-21.
Ren et al., The Use of Proteomics in the Discovery of Serum Biomarkers from Patients with Severe Acute Respiratory Syndrome. Proteomics. 2004; 4(11):3477-84.
Soares et al., Proteômica e sepse. Novas Perspectivas Para O Diagnóstico. Revista Brasileira de Terapia Intensiva. São Paulo, BR. 2007; 19(1):14-22.
Suri et al., Diagnostic and prognostic utility of C-reactive protein, alpha-1-antitrypsin and alpha-2-macroglobulin in neonatal sepsis: a comparative account. Indian Pediatr. 1991; 28(10): 1159-64.
Ulrike et al., Matrilysin is much more efficient than other matrix metalloproteinases in the proteolytic inactivation of alpha 1-antitrypsin. Biochem Biophys Res Commun. 1994; 204: 613-20.
Vissers et al., Cleavage and inactivation of alpha 1-antitrypsin by metalloproteinases released from neutrophils. J Clin Invest. 1988; 82(2): 706-11.
First Office Action dated May 18, 2015 by the State Intellectual Property Office of the People's Republic of China for Chinese Patent Application No. 201280067006.X, which was filed on Nov. 14, 2012 and published as CN 104204808 on Dec. 10, 2014 (Applicant—Universitätsklinikum Jena) (12 pages).
International Search Report dated Mar. 6, 2013 for International Patent Application No. PCT/EP2012/072644, which was filed on Mar. 6, 2013 and published as WO 2013/072381 on May 23, 2013 (Inventor—Kiehntopf et al.; Applicant—Universitätsklinikum Jena) (6 pages).
Written Opinion dated May 14, 2014 for International Patent Application No. PCT/EP2012/072644, which was filed on Mar. 6, 2013 and published as WO 2013/072381 on May 23, 2013 (Inventor—Kiehntopf et al.; Applicant—Universitätsklinikum Jena) (8 pages).
International Preliminary Report on Patentability dated May 20, 2014 for International Patent Application No. PCT/EP2012/072644, which was filed on Mar. 6, 2013 and published as WO 2013/072381 on May 23, 2013 (Inventor—Kiehntopf et al.; Applicant—Universitätsklinikum Jena) (9 pages).
Preliminary Amendment filed on May 14, 2014 with the U.S. Patent and Trademark Office for U.S. Appl. No. 13/261,860, filed May 14, 2014 and published as US 2014/0248631 on Sep. 4, 2014 (Inventor—Kiehntopf et al.; Applicant—Universitätsklinikum Jena) (3 pages).
Preliminary Amendment filed on Jul. 11, 2014 with the U.S. Patent and Trademark Office for U.S. Appl. No. 13/261,860, filed May 14, 2014 and published as US 2014/0248631 on Sep. 4, 2014 (Inventor—Kiehntopf et al.; Applicant—Universitätsklinikum Jena) (8 pages).
Restriction Requirement dated Nov. 3, 2015 by the U.S. Patent and Trademark Office for U.S. Appl. No. 13/261,860, filed May 14, 2014 and published as US 2014/0248631 on Sep. 4, 2014 (Inventor—Kiehntopf et al.; Applicant—Universitätsklinikum Jena) (8 pages).
Response to Restriction Requirement filed on Dec. 18, 2015 by the U.S. Patent and Trademark Office for U.S. Appl. No. 13/261,860, filed May 14, 2014 and published as US 2014/0248631 on Sep. 4, 2014 (Inventor—Kiehntopf et al.; Applicant—Universitätsklinikum Jena) (8 pages).
Non-Final Office Action dated Feb. 5, 2016 by the U.S. Patent and Trademark Office for U.S. Appl. No. 13/261,860, filed May 14, 2014 and published as US 2014/0248631 on Sep. 4, 2014 (Inventor—Kiehntopf et al.; Applicant—Universitätsklinikum Jena) (26 pages).
Response to Non-Final Office Action filed on May 4, 2016 with the U.S. Patent and Trademark Office for U.S. Appl. No. 13/261,860, filed May 14, 2014 and published as US 2014/0248631 on Sep. 4, 2014 (Inventor—Kiehntopf et al.; Applicant—Universitätsklinikum Jena) (18 pages).
Final Office Action dated Jun. 10, 2016 by the U.S. Patent and Trademark Office for U.S. Appl. No. 13/261,860, filed May 14, 2014 and published as US 2014/0248631 on Sep. 4, 2014 (Inventor—Kiehntopf et al.; Applicant—Universitätsklinikum Jena) (16 pages).
Response After Final Office Action filed on Aug. 5, 2016 with the U.S. Patent and Trademark Office for U.S. Appl. No. 13/261,860, filed May 14, 2014 and published as US 2014/0248631 on Sep. 4, 2014 (Inventor—Kiehntopf et al.; Applicant—Universitätsklinikum Jena) (28 pages).
Advisory Action dated Aug. 11, 2016 by the U.S. Patent and Trademark Office for U.S. Appl. No. 13/261,860, filed May 14, 2014 and published as US 2014/0248631 on Sep. 4, 2014 (Inventor—Kiehntopf et al.; Applicant—Universitätsklinikum Jena) (5 pages).
Notice of Abandonment dated Dec. 23, 2016 by the U.S. Patent and Trademark Office for U.S. Appl. No. 13/261,860, filed May 14, 2014 and published as US 2014/0248631 on Sep. 4, 2014 (Inventor—Kiehntopf et al.; Applicant—Universitätsklinikum Jena) (2 pages).

\* cited by examiner

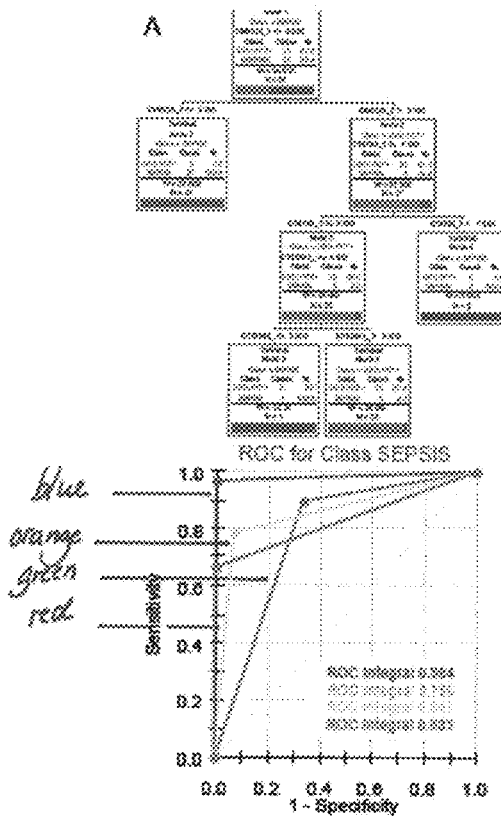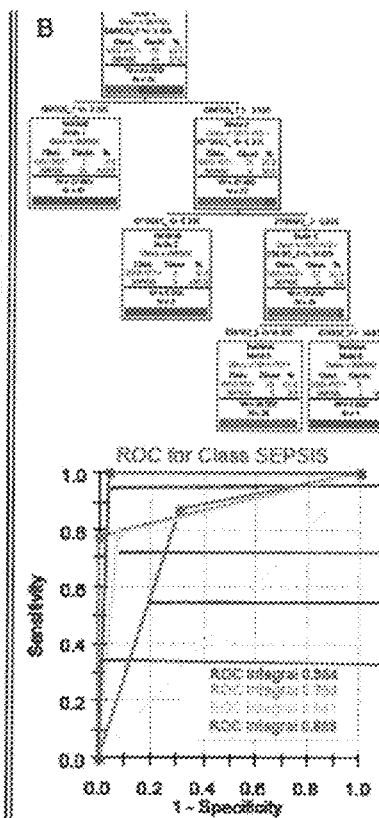
FIG. 1A  FIG. 1B
FIG. 1C

FIG. 4A
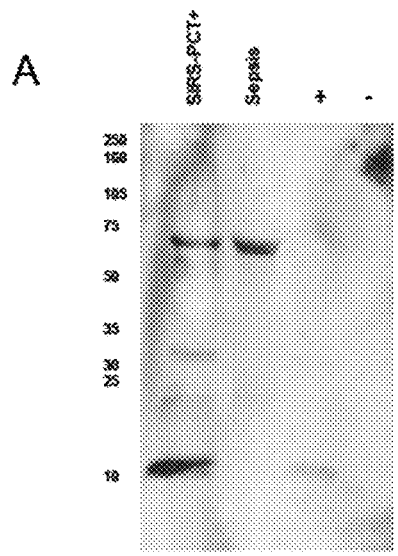
FIG. 4B
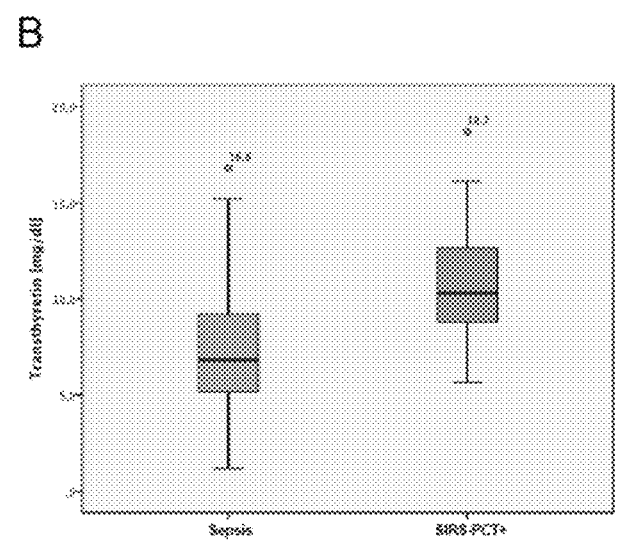
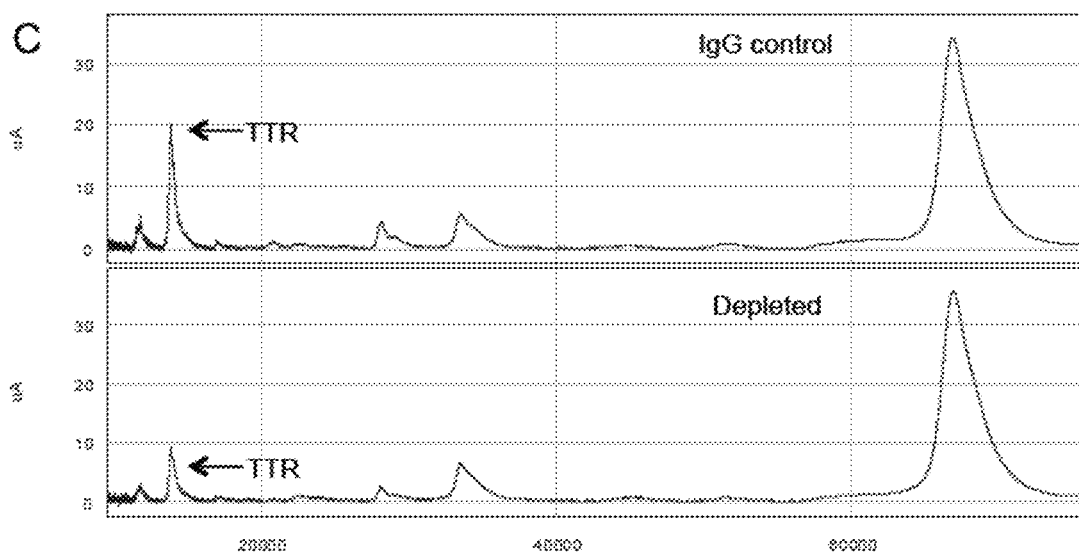
FIG. 4C

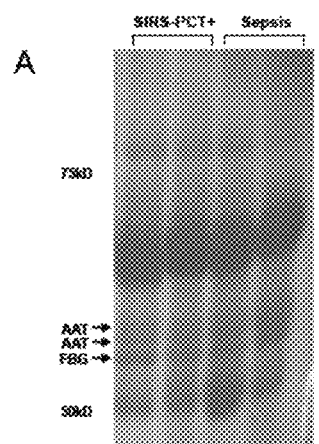
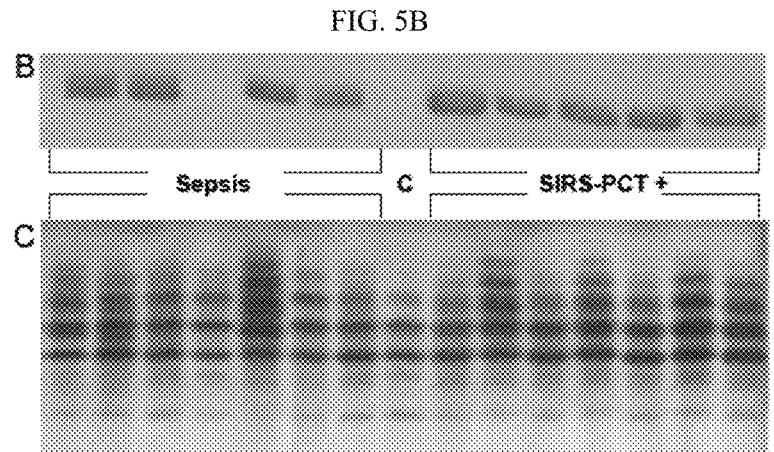
FIG. 5A
FIG. 5B
FIG. 5C
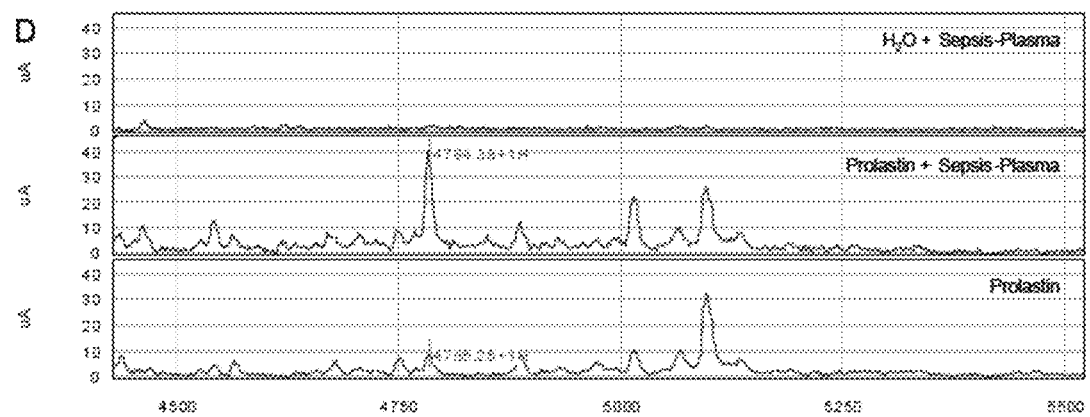
FIG. 5D
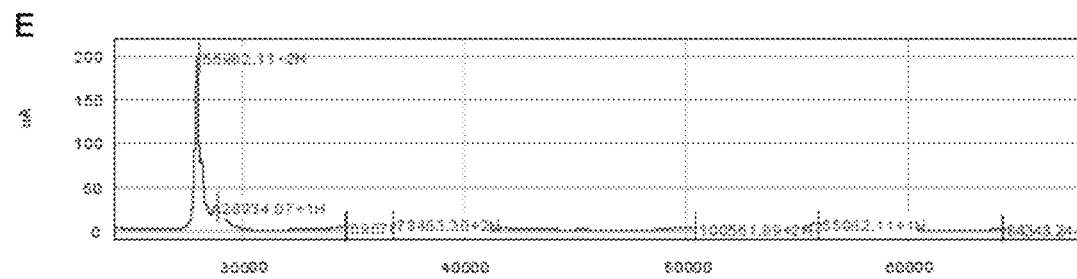
FIG. 5E

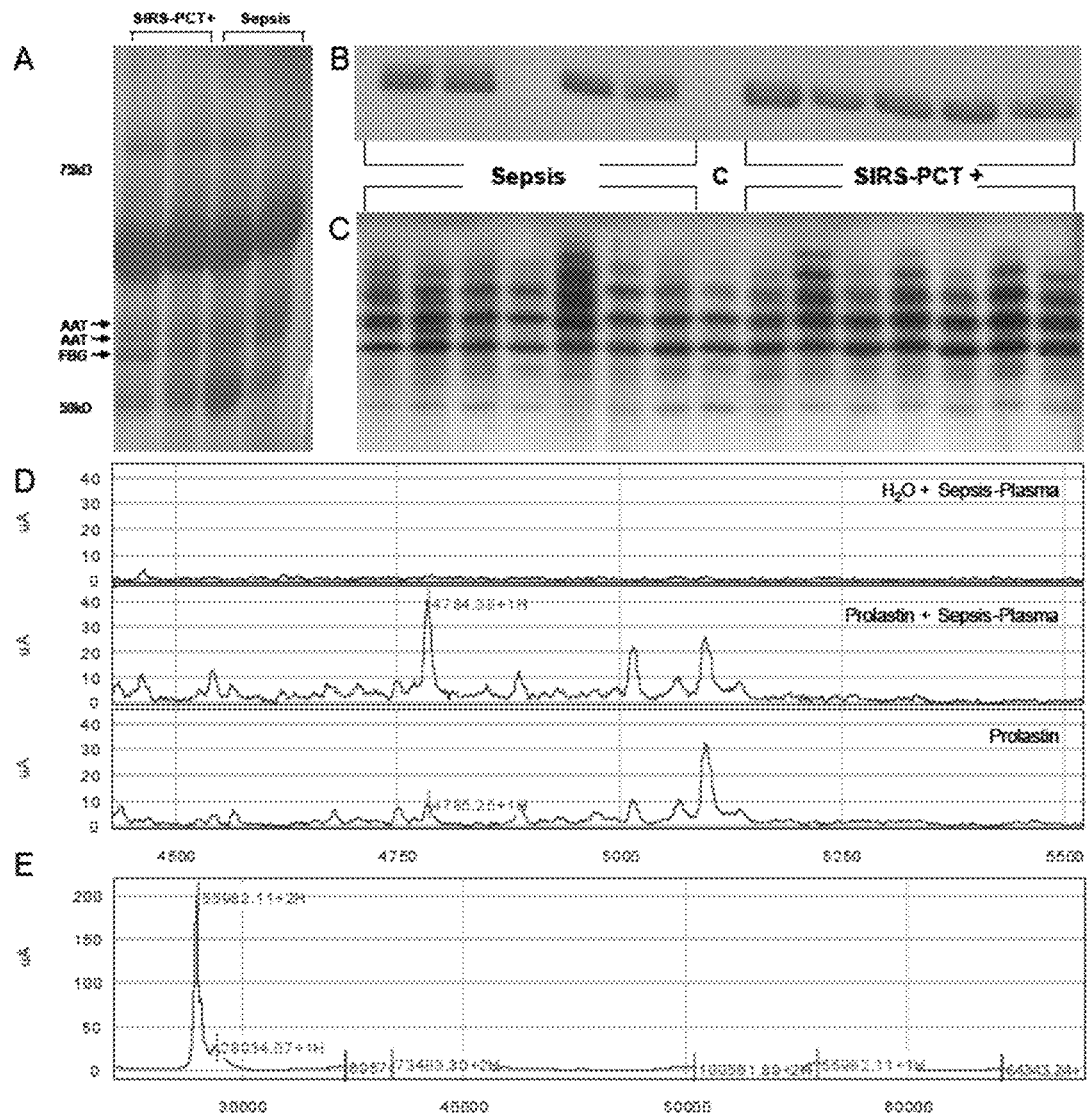
FIG. 5A, FIG. 5B, FIG. 5C, FIG. 5D, FIG. 5E
FIG. 6
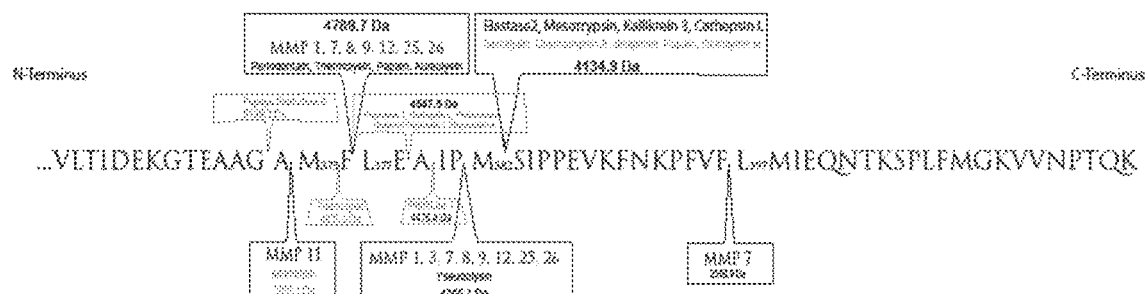

FIG 9:

α1-Antitrypsin

Complete amino acid sequence (N- to C-terminal): (SEQ ID NO: 1)

```
         10         20         30         40         50         60
  EDPQGD AAQKTDTSHH DDDHPTFNKI TPNLAEFAFS
         70         80         90        100        110        120
  LYRQLAHQSN STNIFFSPVS IATAFAMLSL GTKADTHDEI LEGLNFNLTE IPEAQIHEGF
        130        140        150        160        170        180
  QELLRTLNQP DSQLQLTTGN GLFLSEGLKL VDKFLEDVKK LYHSEAFTVN FGDTEEAKKQ
        190        200        210        220        230        240
  INDYVEKGTQ GKIVDLVKEL DRDTVFALVN YIFFKGKWER PFEVKDTEEE DFHVDQVTTV
        250        260        270        280        290        300
  KVPMMKRLGM FNIQHCKKLS SWVLLMKYLG NATAIFFLPD EGKLQHLENE LTHDIITKFL
        310        320        330        340        350        360
  ENEDRRSASL HLPKLSITGT YDLKSVLGQL GITKVFSNGA DLSGVTEEAP LKLSKAVHKA
        370        380        390        400        410
  VLTIDEKGTE AAGAMFLEAI PMSIPPEVKF NKPFVFLMIE QNTKSPLFMG KVVNPTQK
```

Fragments:

| Grade | Size (Dalton) | Cleavage Site | Sequence | SEQ ID NO: |
|---|---|---|---|---|
| 6 | 2503.9 | $F_{396}-L_{397}$ | LMIE QNTKSPLFMG KVVNPTQK | 2 |
| 4 | 4047.8 | $S_{383}-I_{384}$ | IPPEVKF NKPFVFLMIE QNTKSPLFMG KVVNPTQK | 3 |
| 2 | 4134.9 | $M_{382}-S_{383}$ | SIPPEVKF NKPFVFLMIE QNTKSPLFMG KVVNPTQK | 4 |
| 3 | 4266.1 | $P_{381}-M_{382}$ | MSIPPEVKF NKPFVFLMIE QNTKSPLFMG KVVNPTQK | 5 |
| 5 | 4363.2 | $I_{380}-P_{381}$ | PMSIPPEVKF NKPFVFLMIE QNTKSPLFMG KVVNPTQK | 6 |
| 3 | 4476.4 | $A_{379}-I_{380}$ | I PMSIPPEVKF NKPFVFLMIE QNTKSPLFMG KVVNPTQK | 7 |
| 4 | 4547.5 | $E_{378}-A_{379}$ | AI PMSIPPEVKF NKPFVFLMIE QNTKSPLFMG KVVNPTQK | 8 |
| 5 | 4676.6 | $L_{377}-E_{378}$ | EAI PMSIPPEVKF NKPFVFLMIE QNTKSPLFMG KVVNPTQK | 9 |
| 1 | 4789.7 | $F_{376}-L_{377}$ | LEAI PMSIPPEVKF NKPFVFLMIE QNTKSPLFMG KVVNPTQK | 10 |
| 6 | 4936.9 | $M_{375}-F_{376}$ | FLEAI PMSIPPEVKF NKPFVFLMIE QNTKSPLFMG KVVNPTQK | 11 |
| 5 | 5068.1 | $A_{374}-M_{375}$ | MFLEAI PMSIPPEVKF NKPFVFLMIE QNTKSPLFMG KVVNPTQK | 12 |
| 6 | 5139.2 | $G_{373}-A_{374}$ | AMFLEAI PMSIPPEVKF NKPFVFLMIE QNTKSPLFMG KVVNPTQK | 13 |
| 1 | ca. 50000 (N-terminal) | $F_{376}-L_{377}$ | MPSSVSWGIL LAGLCCLVP VSLAEDPQGD AAQKTDTSHH DQDHPTFNKI TPNLAEFAFS LYRQLAHQSN STNIFFSPVS IATAFAMLSL GTKADTHDEI LEGLNFNLTE IPEAQIHEGF QELLRTLNQP DSQLQLTTGN GLFLSEGLKL VDKFLEDVKK LYHSEAFTVN FGDTEEAKKQ INDYVEKGTQ GKIVDLVKEL DRDTVFALVN YIFFKGKWER PFEVKDTEEE DFHVDQVTTV KVPMMKRLGM FNIQHCKKLS SWVLLMKYLG NATAIFFLPD EGKLQHLENE LTHDIITKFL ENEDRRSASL HLPKLSITGT YDLKSVLGQL GITKVFSNGA DLSGVTEEAP LKLSKAVHKA VLTIDEKGTE AAGAMF | 15 |

DIAGNOSIS OF SEPSIS AND SYSTEMIC INFLAMMATORY RESPONSE SYNDROME

CROSS-REFERENCE TO RELATED PATENT APPLICATIONS

This application is a continuation application of U.S. patent application Ser. No. 13/261,860 (now abandoned) filed May 14, 2014, which is a national phase application of International Application No. PCT/EP2012/072644 filed Nov. 14, 2012, which claims the benefit of the filing date of EP Application No. 11189024.0, which was filed on Nov. 14, 2011. The content of these earlier filed applications is hereby incorporated by reference herein in its entirety.

SEQUENCE LISTING

The Sequence Listing submitted herewith as a text file named "37578_00336U2_Sequence_Listing," created on Dec. 7, 2016, and having a size of 16,384 bytes is hereby incorporated by reference pursuant to 37 C.F.R. § 1.52(e)(5).

FIELD OF THE INVENTION

The present invention is in the field of medicine, more in particular diagnostics and even more in particular the diagnosis and prognosis of sepsis.

BACKGROUND

The present invention relates to the diagnosis of septic complications. The term "sepsis" has been used to describe a variety of clinical conditions related to systemic manifestations of inflammation accompanied by an infection. Because of clinical similarities to inflammatory responses secondary to non-infectious aetiologies, identifying sepsis has been a particularly challenging diagnostic problem. In this respect, definitions have been provided for "Systemic Inflammatory Response Syndrome" (or "SIRS"), which refers generally to a severe systemic response to an infectious or non-infectious insult, and for the related syndromes "sepsis," "severe sepsis," and "septic shock" (Bone et al., Chest 101:1644-53, 1992). SIRS may be related to both infection and to numerous non-infective aetiologies, including trauma.

Despite the availability of antibiotics and supportive therapy, sepsis represents a significant cause of morbidity and mortality. Several laboratory tests have been investigated for use, in conjunction with a complete clinical examination of a subject, for the diagnosis/prognosis of sepsis (Giamarellos-Bourboulis et al., Intensive Care Med. 28: 1351-56, 2002).

Several molecular markers have been discussed to facilitate diagnosis and treatment monitoring of sepsis in humans and several animal species. The most widely used ones may be CRP (C-reactive protein) and PCT (procalcitonin).

Also various interleukins have been discussed as potential biomarkers of sepsis. However they are of limited use at present because of a lack of specificity. For example, Carrigan et al. (Clinical Chemistry 50 (8) (2004) 1301-1314) reported the following sensitivities and specificities for these markers in humans:

TABLE 1

ROC analysis results for various biomarker-based prediction of sepsis in adult and neonatal cases.[a]

| Marker | Age group | Cutoff range | Sensitivity, % | Specificity, % | Referenced studies |
|---|---|---|---|---|---|
| TNFα | Adults | 11.5 ng/L | 55 | 66 | (38) |
|  | Neonates | 12-20 ng/L | 67/79/88 | 43/71/86 | (23, 61 63) |
| IL-6 | Adults | 50-200 ng/L | 51/67/86 | 53/65/79 | (30, 35, 36, 66) |
|  | Neonates | 10-160 ng/L | 71/84/100 | 43/71/96 | (26, 29, 61, 63, 70-72) |
| IL-1ra | Children | NA[b] | 33 | 89 | (85) |
|  | Neonates | 10.9 µg/L | 93 | 92 | (70) |
| IL-8 | Adults | 30-340 ng/L | 57/63/68 | 57/76/93 | (30, 35, 85) |
|  | Neonates | 50 ng/L | 92 | 70 | (61) |
| CRP | Adults | 4-150 mg/L | 35/69/89 | 18/61/81 | (30, 35, 36, 38, 46 66, 88, 89) |
|  | Neonates | 1-23 mg/L | 43/65/96 | 80/90/100 | (22, 26, 63, 70, 89, 90) |
| PCT | Adults | 0.4-81 µg/L | 65/81/97 | 48/73/94 | (30, 35-38, 43, 46, 66, 88, 89, 122, 123) |
|  | Neonates | 1.0-61 µg/L | 77/85/99 | 62/83/91 | (22, 72, 89, 90) |

[a]Values listed are for differentiating infected individuals from uninfected controls rather than from healthy individuals.
Sensitivities and specificities Ested are minimum, mean [in bold], and maximum percentages.
[b]NA. not avalable.

This overview may be found in EP 2 060 920 A1.

These data show that even in humans, where septic disease patterns are extensively investigated, sensitivity and specificity of current markers can (even as mean values) come down to as low as 33% and 66% respectively, not to mention the in homogeneity of presently published data.

These data show that there is definitely a need for new diagnostic markers with improved diagnostic characteristics. Therefore, the diagnosis of sepsis, especially early diagnosis of sepsis, is still a great need in clinical medicine. An optimum diagnosis should reveal persons with a risk of developing sepsis or persons being at an early stage of sepsis. Specifically in systemic inflammation, i.e. in multiply traumatized patients such a diagnosis is often very difficult because of other pathological processes interfering with the "normal" physiological values and parameters measured in standard intensive care medicine.

Diagnosis of sepsis in patients with systemic inflammation, e.g. complications in polytraumatised patients is a very specific problem for which a high need exists in intensive care medicine.

It is therefore an object of the present invention to provide a suitable method for diagnosing sepsis, being sensitive and/or specific.

Definitions

The terms "sepsis" or "septic complications" are used synonymously in the present application and are understood to encompass "sepsis", "septic complications", "severe sepsis", "septic shock", and even earlier stages thereof, all symptoms being related to systemic manifestations of inflammation accompanied by an infection.

Herein, "Systemic Inflammatory Response Syndrome" (or "SIRS") is defined as the systemic inflammatory response to a variety of severe clinical insults manifested by two or more of the following conditions: 1) temperature>38° C. or <36° C.; 2) heart rate>90 beats per minute; 3) respiratory rate>20 breaths per minute or PaCO2<32 mm Hg; and 4) white blood cell count>12,000/cu mm; <4,000/cu mm, or >10% immature (band) forms. When SIRS is the result of a confirmed infectious process, it is termed sepsis (Bone R C, Balk R A, Cerra F B, Dellinger R P, Fein A M, Knaus W A, et al. Definitions for sepsis and organ failure and guidelines for the use of innovative therapies in sepsis. The ACCP/SCCM Consensus Conference Committee. American College of Chest Physicians/Society of Critical Care Medicine. Chest. 1992 June; 101(6):1644-1655.)

Herein, "alpha-1-antitrypsin" is also referred to as antitrypsin and "ATT". Alpha-1-Antitrypsin or α-1-antitrypsin (A1AT) is a protease inhibitor belonging to the serpin superfamily. It is generally known as serum trypsin inhibitor. Alpha-1-antitrypsin is also referred to as alpha-1-proteinase inhibitor (A1PI) because it inhibits a wide variety of proteases. It protects tissues from enzymes of inflammatory cells, especially neutrophil elastase, and has a reference range in blood of 1.5-3.5 g/l, but the concentration can rise manyfold upon acute inflammation. In its absence, neutrophil elastase is free to break down elastin, which contributes to the elasticity of the lungs, resulting in respiratory complications such as emphysema, or COPD (chronic obstructive pulmonary disease) in adults and cirrhosis in adults or children.

Herein, "transthyretin" (TTR) is a serum and cerebrospinal fluid carrier of the thyroid hormone thyroxine (T4) and retinol. This is how transthyretin gained its name, transports thyroxine and retinol. TTR was originally called prealbumin because it ran faster than albumins on electrophoresis gels. The discriminatory peak of TTR is at 13.8 kDa and claimed herein in the context of the methods and kits claimed.

In the context of the present invention, the terms "threshold", "threshold value", "cut-off" and "cut-off value" are used synonymously.

The term "correlating," as used herein in reference to the use of diagnostic and prognostic markers, refers to comparing the presence or amount of the marker(s) in a patient to its presence or amount in persons known to suffer from, or known to be at risk of, a given condition; or in persons known to be free of a given condition. As discussed above, a marker level in a patient sample can be compared to a level known to be associated with a specific diagnosis. The sample's marker level is said to have been correlated with a diagnosis; that is, the skilled artisan can use the marker level to determine whether the patient suffers from a specific type diagnosis, and respond accordingly. Alternatively, the sample's marker level can be compared to a marker level known to be associated with a good outcome (e.g., the absence of disease, etc.). In preferred embodiments, a profile of marker levels is correlated to a global probability or a particular outcome.

A "prognosis" refers to assignment of a probability that a given course or outcome will occur. This is often determined by examining one or more "prognostic indicators". These are markers, the presence or amount of which in a patient (or a sample obtained from the patient) signal a probability that a given course or outcome will occur. For example, when one or more prognostic indicators reach a sufficiently high level in samples obtained from such patients, the level may signal that the patient is at an increased probability for eventually advancing into end-stage renal disease (ESRD), i.e. the patient has an increased probability of being a "progressor".

DETAILED DESCRIPTION OF THE INVENTION

The present invention relates to a method for the diagnosis, prediction or risk stratification for mortality and/or disease outcome of a subject that has or is suspected to have sepsis, comprising determining the antitrypsin (ATT) or fragments thereof in a sample taken from said subject and/or determining presence and/or level of transthyretin (TTR) or fragments thereof, wherein the presence and/or level of ATT and/or TTR or fragments thereof is correlated with an increased risk of mortality and/or poor disease outcome; and, wherein said increased risk of mortality and/or poor disease outcome is given if the presence and/or level of ATT (the mature fragment; 55 kDa) is below a certain cut-off value and/or the level of fragments thereof is above a certain cut-off value and/or said increased risk of mortality and/or poor disease outcome is given if the presence and/or level of TTR is below a certain cut-off value and/or the level of fragments thereof is below a certain cut-off value.

The fragments are those shown in FIG. 9.

The invention also relates in general to the use of ATT and/or TTR or its fragments for the diagnosis of sepsis.

Numerous proteases digest α-1-Antitrypsin in the reactive center loop at the c-terminus. A-1-Antitrypsin fragments are produced (see Figures). SELDI-TOF-MS (surface enhanced laser desorption ionization-time of flight-mass spectrometry) is claimed as one method for analysing and/or determining the presence and/or levels of these fragments in the context of the invention.

240 patients with infectious sepsis or SIRS were analysed. The 4789.7 Da α-1-antitrypsin-fragment as claimed by the present invention distinguishes as one marker to differentiate between SIRS and sepsis in general.

The method according to the invention also involves comparing the level of marker for the individual/patient/ subject to be diagnosed with a predetermined value. The predetermined value can take a variety of forms. It can be a single cut-off value: This can be for instance a median or mean or the $75^{th}$, $90^{th}$, $95^{th}$ or $99^{th}$ percentile of a reference population. This can be for instance also an "optimal" cut-off value. The optimal cut-off value for a given marker is the value where the product of diagnostic sensitivity and specificity is maximal for this marker. Diagnostic sensitivity is the relative fraction of patients, carrying the disease or the risk for developing the disease (depending on the diagnostic or prognostic question to be answered in any particular case), which are correctly recognized as such by a marker ("true positives"), and the diagnostic specificity is the relative fraction of patients, not carrying the disease or the risk for developing the disease (depending on the diagnostic or prognostic question to be answered in any particular case), which are recognized as such by a marker ("true negatives"). This can by a cut-off value optimized for a maximal negative predictive value or maximal positive predictive value, depending on clinical or economical needs. Thereby optimizing specificity and sensitivity.

Thus, one might adopt the cut-off value depending on whether it is considered more appropriate to identify most of the subjects at risk at the expense of also identifying "false positives", or whether it is considered more appropriate to identify mainly the subjects at high risk at the expense of missing several subjects at moderate risk.

The predetermined value can be established based upon comparative groups, such as where the risk in one defined group is double the risk in another defined group. It can be a range, for example, where the tested population is divided equally (or unequally) into groups, such as a low-risk group, a medium-risk group and a high-risk group, or into quartiles, the lowest quartile being individuals with the lowest risk and the highest quartile being individuals with the highest risk.

The predetermined value can vary among particular reference populations selected, depending on their habits, ethnicity, genetics etc. Accordingly, the predetermined values selected may take into account the category in which an individual falls. Appropriate ranges and categories can be selected with no more than routine experimentation by those of ordinary skill in the art.

In certain embodiments, particular thresholds for one or more markers in a panel are not relied upon to determine if a profile of marker levels obtained from a subject are indicative of a particular diagnosis/prognosis. Rather, the present invention may utilize an evaluation of a marker panel "profile" as a unitary whole. A particular "fingerprint" pattern of changes in such a panel of markers may, in effect, act as a specific diagnostic or prognostic indicator. As discussed herein, that pattern of changes may be obtained from a single sample, or from temporal changes in one or more members of the panel (or a panel response value). A panel herein refers to a set of markers. Herein, one of the known markers may be combined with ATT and/or TTR.

A panel response value can be derived by various methods. One example is Cox proportional hazards analysis. Another example is optimizing ROC curves: This can be achieved by plotting ROC curves for the sensitivity of a particular panel of markers versus 1-(specificity) for the panel at various cut-offs.

In these methods, a profile of marker measurements from a subject is considered together to provide a global probability (expressed either as a numeric score or as a percentage risk) of a diagnosis or prognosis. In such embodiments, an increase in a certain subset of markers may be sufficient to indicate a particular diagnosis/prognosis in one patient, while an increase in a different subset of markers may be sufficient to indicate the same or a different diagnosis/prognosis in another patient. Weighting factors may also be applied to one or more markers in a panel, for example, when a marker is of particularly high utility in identifying a particular diagnosis/prognosis, it may be weighted so that at a given level it alone is sufficient to signal a positive result. Likewise, a weighting factor may provide that no given level of a particular marker is sufficient to signal a positive result, but only signals a result when another marker also contributes to the analysis.

In certain embodiments, markers and/or marker panels are selected to exhibit at least about 70% sensitivity, more preferably at least about 80% sensitivity, even more preferably at least about 85% sensitivity, still more preferably at least about 90% sensitivity, and most preferably at least about 95% sensitivity, combined with at least about 70% specificity, more preferably at least about 80% specificity, even more preferably at least about 85% specificity, still more preferably at least about 90% specificity, and most preferably at least about 95% specificity. In particularly preferred embodiments, both the sensitivity and specificity are at least about 75%, more preferably at least about 80%, even more preferably at least about 85%, still more preferably at least about 90%, and most preferably at least about 95%. The term "about" in this context refers to +/−5% of a given measurement.

In other embodiments, a positive likelihood ratio, negative likelihood ratio, odds ratio, or hazard ratio is used as a measure of a test's ability to predict risk or diagnose a disease. In the case of a positive likelihood ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In the case of a negative likelihood ratio, a value of 1 indicates that a negative result is equally likely among subjects in both the "diseased" and "control" groups; a value greater than 1 indicates that a negative result is more likely in the test group; and a value less than 1 indicates that a negative result is more likely in the control group. In certain preferred embodiments, markers and/or marker panels are preferably selected to exhibit a positive or negative likelihood ratio of at least about 1.5 or more or about 0.67 or less, more preferably at least about 2 or more or about 0.5 or less, still more preferably at least about 5 or more or about 0.2 or less, even more preferably at least about 10 or more or about 0.1 or less, and most preferably at least about 20 or more or about 0.05 or less. The term "about" in this context refers to +/−5% of a given measurement.

In the case of an odds ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In certain preferred embodiments, markers and/or marker panels are preferably selected to exhibit an odds ratio of at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less. The term "about" in this context refers to +/−5% of a given measurement.

In the case of a hazard ratio, a value of 1 indicates that the relative risk of an endpoint (e.g., death) is equal in both the "diseased" and "control" groups; a value greater than 1 indicates that the risk is greater in the diseased group; and a value less than 1 indicates that the risk is greater in the control group. In certain preferred embodiments, markers and/or marker panels are preferably selected to exhibit a hazard ratio of at least about 1.1 or more or about 0.91 or less, more preferably at least about 1.25 or more or about 0.8 or less, still more preferably at least about 1.5 or more or about 0.67 or less, even more preferably at least about 2 or more or about 0.5 or less, and most preferably at least about 2.5 or more or about 0.4 or less. The term "about" in this context refers to +/5% of a given measurement.

The skilled artisan will understand that associating a diagnostic or prognostic indicator, with a diagnosis or with a prognostic risk of a future clinical outcome is a statistical analysis. For example, a marker level of greater than X may signal that a patient is more likely to suffer from an adverse outcome than patients with a level less than or equal to X, as determined by a level of statistical significance. Additionally, a change in marker concentration from baseline levels may be reflective of patient prognosis, and the degree of change in marker level may be related to the severity of adverse events. Statistical significance is often determined by comparing two or more populations, and determining a confidence interval and/or a p value. See, e.g., Dowdy and Wearden, Statistics for Research, John Wiley & Sons, New York, 1983. Preferred confidence intervals of the invention are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

In yet other embodiments, multiple determinations of diagnostic or prognostic markers can be made, and a temporal change in the marker can be used to determine a diagnosis or prognosis. For example, a marker concentration in a subject sample may be determined at an initial time, and again at a second time from a second subject sample. In such embodiments, an increase in the marker from the initial time to the second time may be indicative of a particular diagnosis, or a particular prognosis. Likewise, a decrease in the marker from the initial time to the second time may be indicative of a particular diagnosis, or a particular prognosis.

The term "sample" as used herein refers to a sample of bodily fluid obtained for the purpose of diagnosis, prognosis, or evaluation of a subject of interest, such as a patient.

Preferred test samples include blood, serum, plasma, cerebrospinal fluid, urine, saliva, sputum, and pleural effusions. In addition, one of skill in the art would realize that some test samples would be more readily analyzed following a fractionation or purification procedure, for example, separation of whole blood into serum or plasma components.

Thus, in a preferred embodiment of the method according to the invention said sample is selected from the group comprising a blood sample, a serum sample, a plasma sample, and a urine sample or an extract of any of the aforementioned samples.

In a preferred embodiment of the invention the level of ATT and/or TTR or fragments thereof may preferably be correlated with the prediction or risk stratification for mortality and/or disease outcome by a method which may be selected from the following group of alternatives:
  correlation with respect to the median of the level of ATT and/or fragments thereof in an ensemble of pre-determined samples,
  correlation with respect to quantiles of the level of ATT and/or fragments thereof in an ensemble of pre-determined samples, and
  correlation with a mathematical model, such as for example Cox Regression.

Preferably, the cut-off value of ATT is about 2 g/l, and may deviate depending on the patient analysed by about 5%, 10% or even 20%.

Preferably, the cut-off value of ATT fragments is about 4.18 pmol/µl, e.g. fragment 4789.7 (SEQ ID NO. 10 Table 3; PMSIPPEVKFNKPFVFLMIEQNTKSPLFMGKV-VNPTQK) corresponding to 20 ng/µl, and fragment 50 kD (4.18 pmol/µl) may deviate depending on the patient analysed by about 5%, 10% or even 20%.

The cut-off value of TTR is about 10 mg/dl (see FIG. 4), and may deviate depending on the patient analysed by about 5%, 10% or even 20%

According to the invention the level of ATT or fragments thereof and/or TTR or fragments thereof associated with an increased risk for mortality is
  for ATT below the median level of the normal population and/or
  for ATT fragments above the median level of the normal population and/or
  for TTR is below the median level of the normal population.

The claimed method may further comprise the following steps:
  taking a sample from a subject, and/or
  determining the level of ATT or fragments thereof, and/or
  determining the level of TTR or fragments thereof, and/or
  correlating the level of ATT or fragments and/or TTR or fragments thereof with a perquantile risk of mortality or survival.

The invention relates to a method, wherein a sample is taken at one or more of the following time points, when the subject is first admitted to a medical institution or in the ambulance, when the subject is in the emergency room, when the subject is in the intensive care unit, before treatment, after initiation of treatment, 24 hours after initiation of treatment, 48 hours after initiation of treatment, and/or 72 hours after initiation of treatment and/or thereafter such as 10 days, 14 days or even 20 days.

The subject is under a condition selected from the group comprising: an infection requiring antimicrobial therapy, escalated forms of infection like sepsis, severe sepsis and septic shock.

In addition to prediction or risk stratification for mortality and/or disease outcome of said subject the determination of ATT or fragments thereof and/or of TTR or fragments thereof in a sample taken from said subject, is used herein to differentially diagnose whether said subject is likely to have systemic inflammation (SIRS), initial sepsis, severe sepsis or septic shock.

The said sample is preferably selected from a group comprising a plasma sample, a serum sample, a whole blood sample, a blood sample or fractions thereof, a lymphatic fluid sample, a urine sample and an extract of any of the aforementioned samples.

The level of ATT or fragments thereof and/or TTR or fragments thereof is preferably determined with a diagnostic assay such as an ELISA test or mass-spectrometry or surface enhanced laser desorption ionization-time of flight-mass spectrometry (SELDI-TOF-MS) or LC-MS/MS.

The invention relates to a method of medical decision making for individual patient therapy related to the severity of the disease by monitoring therapy response in a subject with sepsis or a sepsis like disease to a certain drug, comprising the steps of, taking at least two samples from said subject at various time points selected from the group of,
i. before initiation of therapy and/or
ii. after initiation of therapy, and/or
iii. at one or more further time point
determining ATT or fragments thereof and/or TTR or fragments thereof in said sample taken from said subject,
associating the levels of ATT or fragments thereof and/or TTR or fragments thereof in said samples taken from said subject with a positive or a negative response to said certain drug.

Said positive response is given if the level of ATT increases during drug treatment and/or if the level of ATT fragments decreases during drug treatment; and/or said positive response is given if the level of TTR or fragments thereof increases during drug treatment.

The invention preferably relates to a method of medical decision making for individual patient therapy in a subject related to the severity of the disease, comprising the steps of,
taking at least one sample from said subject at various possible time points selected from the group of,
i. before initiation of therapy and/or
ii. after initiation of therapy, and/or
iii. at one or more further time point
determining ATT and/or TTR or fragments thereof in said sample taken from said subject, and
associating the level(s) of ATT and/or TTR or fragments thereof in said samples taken from said subject with the need for a certain therapy.

Said correlation of the level of ATT or fragments thereof to (i) initial sepsis, (ii) severe sepsis or (iii) septic shock is given if the level of ATT is below a certain cut-off value and/or the level of ATT proteolytic fragments is above a certain cut-off value; and/or said correlation of the level of TTR or fragments thereof to (i) initial sepsis, (ii) severe sepsis or (iii) septic shock is given if the level of TTR or fragments thereof is below a certain level.

The invention preferably relates to a method for differentially diagnosing a disease in a subject, wherein the diseases are selected from the group of (i) systemic inflammation (SIRS), (ii) initial sepsis, (iii) severe sepsis or (iv) septic shock, said method comprising the steps of
(1) determining the presence and/or level of ATT and/or TTR or fragments thereof in a sample taken from said subject, and
(2) correlating the presence and/or level of ATT and/or TTR or fragments thereof to (i) initial sepsis, (ii) severe sepsis or (iii) septic shock,
(3) wherein said correlation of the presence and/or level of ATT and/or TTR or fragments thereof to (i) initial sepsis, (ii) severe sepsis or (iii) septic shock is given if the level of ATT is below a certain cut-off value and/or the level of ATT proteolytic fragments is above a certain cut-off value; and/or
(4) wherein said correlation of the presence and/or level of ATT and/or TTR or fragments thereof to (i) initial sepsis, (ii) severe sepsis or (iii) septic shock is given if the level of TTR is below a certain level.

Also, the invention relates to a kit for diagnosis of sepsis and/or predicting the prognosis in a patient with sepsis, comprising, an antibody, an aptamer, or another target specific molecule specific for ATT or fragments thereof and/or TTR or fragments thereof, standard data showing the correlation between the amounts of ATT or fragments thereof contained in samples and prognosis, and a manual.

Also the invention relates to an LC-MS/Ms kit for diagnosing sepsis and/or predicting the prognosis in a patient with sepsis, wherein ATT, TTR or fragments of these re guaranteed by LC-MS/MS. These are compared to standard data sets.

Preferably the following protein is detected (SEQ ID NO. 1). As outlined above and below, in sepsis the ratio of the full length protein to the fragments shown below changes.

TABLE 2

α1-Antitrypsin

```
Complete amino acid sequence (N- to C-terminal; SEQ ID NO. 1)
         10         20         30         40         50         60
MPSSVSWGIL LLAGLCCLVP VSLAEDPQGD AAQKTDTSHH DQDHPTFNKI TPNLAEFAFS
         70         80         90        100        110        120
LYRQLAHQSN STNIFFSPVS IATAFAMLSL GTKADTHDEI LEGLNFNLTE IPEAQIHEGF
        130        140        150        160        170        180
QELLRTLNQP DSQLQLTTGN GLFLSEGLKL VDKFLEDVKK LYHSEAFTVN FGDTEEAKKQ
        190        200        210        220        230        240
INDYVEKGTQ GKIVDLVKEL DRDTVFALVN YIFFKGKWER PFEVKDTEEE DFHVDQVTTV
        250        260        270        280        290        300
KVPMMKRLGM FNIQHCKKLS SWVLLMKYLG NATAIFFLPD EGKLQHLENE LTHDIITKFL
        310        320        330        340        350        360
ENEDRRSASL HLPKLSITGT YDLKSVLGQL GITKVFSNGA DLSGVTEEAP LKLSKAVHKA
        370        380        390        400        410
VLTIDEKGTE AAGAMFLEAI PMSIPPEVKF NKPFVFLMIE QNTKSPLFMG KVVNPTQK SEQ ID NO. 14 is the protein above without the leader and has the
following sequence.
EDPQGD AAQKTDTSHH DQDHPTFNKI TPNLAEFAFS LYRQLAHQSN STNIFFSPVS
IATAFAMLSL GTKADTHDEI LEGLNFNLTE IPEAQIHEGF QELLRTLNQP DSQLQLTTGN
GLFLSEGLKL VDKFLEDVKK LYHSEAFTVN FGDTEEAKKQ INDYVEKGTQ GKIVDLVKEL
DRDTVFALVN YIFFKGKWER PFEVKDTEEE DFHVDQVTTV KVPMMKRLGM FNIQHCKKLS
SWVLLMKYLG NATAIFFLPD EGKLQHLENE LTHDIITKFL ENEDRRSASL HLPKLSITGT
YDLKSVLGQL GITKVFSNGA DLSGVTEEAP LKLSKAVHKA VLTIDEKGTE AAGAMFLEAI
PMSIPPEVKF NKPFVFLMIE QNTKSPLFMG KVVNPTQK
```

TABLE 3

Preferred Fragments:

| SEQ ID NO. | Grade | Size Dalton | Cleavage Site | Sequence |
|---|---|---|---|---|
| 2 | 6 | 2503.9 | $F_{396}-L_{397}$ | LMIE QNTKSPLFMG KVVNPTQK |
| 3 | 4 | 4047.8 | $S_{383}-I_{384}$ | IPPEVKF NKPFVFLMIE QNTKSPLFMG KVVNPTQK |
| 4 | 2 | 4134.9 | $M_{382}-S_{383}$ | SIPPEVKF NKPFVFLMIE QNTKSPLFMG KVVNPTQK |
| 5 | 3 | 4266.1 | $P_{381}-M_{382}$ | MSIPPEVKF NKPFVFLMIE QNTKSPLFMG KVVNPTQK |
| 6 | 5 | 4363.2 | $I_{380}-P_{381}$ | PMSIPPEVKF NKPFVFLMIE QNTKSPLFMG KVVNPTQK |
| 7 | 3 | 4476.4 | $A_{379}-I_{380}$ | I PMSIPPEVKF NKPFVFLMIE QNTKSPLFMG KVVNPTQK |
| 8 | 4 | 4547.5 | $E_{378}-A_{379}$ | AI PMSIPPEVKF NKPFVFLMIE QNTKSPLFMG KVVNPTQK |
| 9 | 5 | 4676.6 | $L_{377}-E_{378}$ | EAI PMSIPPEVKF NKPFVFLMIE QNTKSPLFMG KVVNPTQK |
| 10 | 1 | 4789.7 | $F_{376}-L_{377}$ | LEAI PMSIPPEVKF NKPFVFLMIE QNTKSPLFMG KVVNPTQK |
| 11 | 6 | 4936.9 | $M_{375}-F_{376}$ | FLEAI PMSIPPEVKF NKPFVFLMIE QNTKSPLFMG KVVNPTQK |
| 12 | 5 | 5068.1 | $A_{374}-M_{375}$ | MFLEAI PMSIPPEVKF NKPFVFLMIE QNTKSPLFMG KVVNPTQK |
| 13 | 6 | 5139.2 | $G_{373}-A_{374}$ | AMFLEAI PMSIPPEVKF NKPFVFLMIE QNTKSPLFMG KVVNPTQK |

Table 3 shows fragments of the full length protein. The table also classifies the fragments in more or less preferable for the diagnosis/prognosis of sepsis (see "grade": 1 being very preferable and 6 being only preferable).

SEQ ID NO. 10 is a most preferably used fragment for the methods as outlined above.

SEQ ID NO. 4 may be very preferably used.
SEQ ID NO. 5 and/or 7 may be preferably used.
SEQ ID NO. 3 and/or 8 may be used.
SEQ ID NO. 1, 2, 6, 9, 11, 12, and 13 may also be used.

In the methods outlined above one or more of the fragments may be detected. Any combination of fragments above is hence disclosed and claimed without having to write them all down which the skilled person is able to do.

The present invention also relates to a polypeptide having the sequence of any one of SEQ ID NOS. 2, 3, 4, 5, 6, 7, 8, 9, 10, 11, 12, 13, or 14.

Furthermore, a polynucleotide encoding a polypeptide according to SEQ ID NOS. 2, 3, 4, 5, 6, 7, 8, 9, 10, 11, 12, 13 or 14 is also encompassed.

As the present invention relates to a method comprising the determination of fragments of the recited biomarkers, the invention also relates to substances specifically recognizing these fragments and thereby allowing their determination. In a preferred embodiment said substances are antibodies. Hence, the invention also relates to an antibody specifically binding to a polypeptide having the sequence of any of the SEQ ID NOS. 2, 3, 4, 5, 6, 7, 8, 9, 10, 11, 12, 13 or 14.

Moreover, the invention also relates to the use of a polypeptide according to SEQ ID NO. 1, 2, 3, 4, 5, 6, 7, 8, 9, 10, 11, 12, 13 and/or 14 in a method for diagnosing sepsis, preferably in a method as outlined above.

The invention further relates to a reference standard for AAT fragments produced by a method comprising the step of incubating AAT with MMP-7 under conditions suitable for cleavage. The advantage of this kind of reference standard over an artificial, synthetic reference standard is a closer similarity to in vivo occurring AAT fragments. The reference may be used to determine molecular weight of in vivo molecules identified, to determine the concentration or as any other reference.

BRIEF DESCRIPTION OF THE SEVERAL VIEWS OF THE DRAWINGS

FIGS. 1A-C: Classification of patients with SIRS and sepsis

Classification of patients with noninfectious-caused SIRS (SIRS-PCT+) and patients with sepsis (severe sepsis and septic shock) by two decision tree algorithms and identification of marker CM_6.51 as aprotinin and its relation to Trasylol therapy. FIGS. A and B, Classification trees (top); CM=cluster obtained from CM10 arrays; C1=cluster obtained from Q10 arrays. Receiver operating characteristic curve analysis (middle) and class signification results (bottom) using peak clusters and decision tree algorithms for discrimination of patient groups (sepsis; SIRS-PCT+); blue=training samples, green=blinded test samples, orange=blinded test samples that were reanalyzed 5 months later, red=19 ICU test samples that have been prospectively collected for decision tree validation. FIG. C, Representative profiles of the m/z region adjacent to the marker 6.51 of Trasylol (top), from a single individual with noninfectious caused SIRS (SIRS-PCT+) (middle), and from a single individual with sepsis (bottom) on CM10 chips. Peaks of internal standards used for internal calibration are labeled (arrows).

Figure 2:
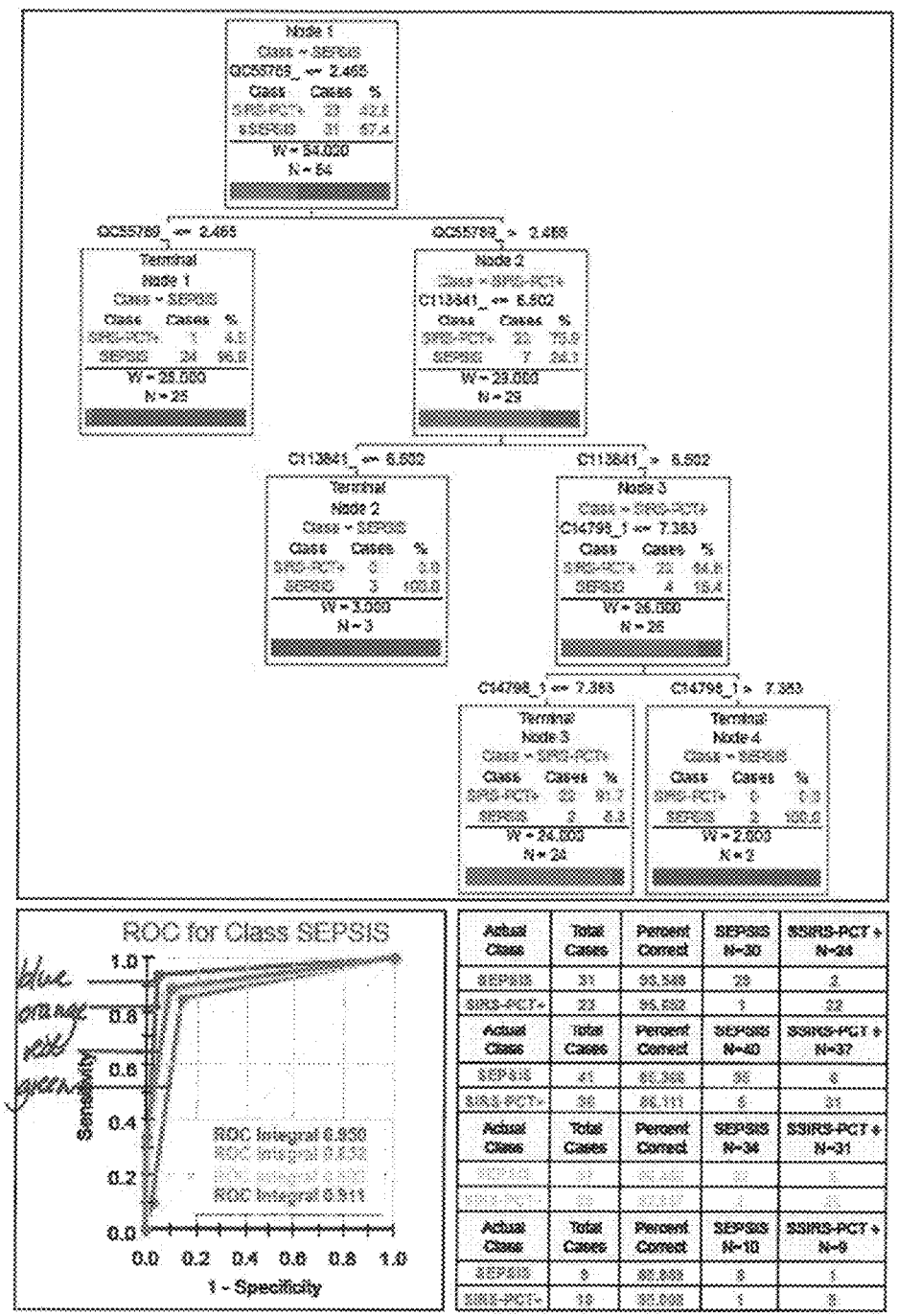

FIG. 2: Second alternative decision tree without consideration of CM_6.51 for classification of patients with non-infectious caused SIRS (SIRS-PCT+) and patients with infectious-caused SIRS (sSEPSIS) (severe sepsis/septic shock) investigated by the decision tree algorithm.

Classification tree; QC and C1=cluster obtained from Q10 arrays (upper panel); ROC curve analysis (lower right panel) and classification results (lower left panel) using peak clusters and the decision tree algorithm for discrimination of patient groups (SIRS-PCT+; sSEPSIS) blue=trainings samples, green=blinded test samples, orange=blinded test samples that were reanalyzed 5 months later, red=19 ICU test samples that have been prospectively collected for decision tree validation.

Figure 3:
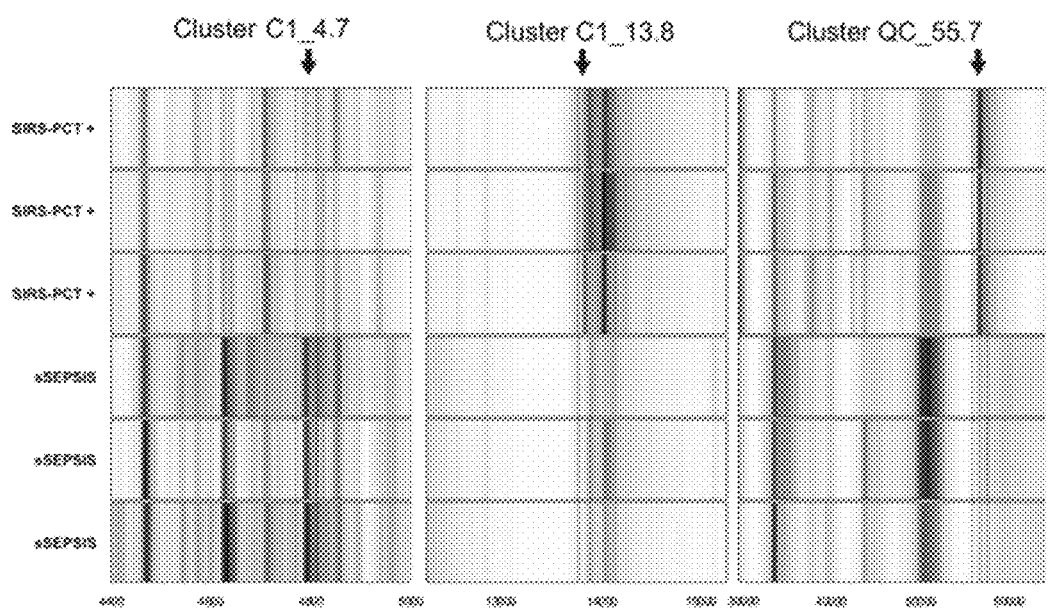

FIG. 3: Representative examples of normalized ProteinChip array profiles of SIRS-PCT+ and sSEPSIS samples Representative examples of normalized ProteinChip array profiles of SIRS-PCT+ and sepsis samples. Representative SELDI-TOF-MS protein pattern from patients of the different investigated groups as illustrated in gel view. Left: Chip type Q10; low range, 4.4 to 5 kd Chip type Q10; peak cluster C1_4.7. Middle: Chip type Q10; middle range, 12.5 to 15 kd; peak cluster C1_13.8. Right: Chip type Q10; high range, 30 to 60 kd; peak cluster QC_55.7. Peak clusters differentiating SIRS-PCT+ and sepsis patients are highlighted by arrows and boxes.

FIGS. 4A-C: Identification and validation of differential expressed peak C1_13.8 as transthyretin (TTR)

FIG. 4A shows the results of Western-blot analysis of TTR; sSIRS=SIRS-PCT+ patient sample; sSEPSIS= sSEPSIS patient sample; +=TTR-positive control; − negative control. FIG. 4B shows the boxplot of TTR concentrations in g/ml of 69 sSEPSIS and 59 SIRS-PCT+ samples FIG. 4C shows the representative normalized ProteinChip Array profiles of samples after immune depletion using either a TTR specific antibody (lower panel) or a control antibody to confirm the affiliation of TTR with the differentially expressed marker C1_13.8.

FIGS. 5A-E: Purification and identification of QC_55.7 and C1_4.7

FIG. 5A: 10% Maxi-PAGE of SIRS-PCT+ and sSEPSIS samples showing three spots that have been identified as alpha-1-antitrypsin (AAT) and fibrinogen (FBG) by in-gel digestion, MS- and MALDI-TOF/TOF analysis. FIG. 5B: Anti AAT-Western-Blot showing that AAT is present in two isoforms with the lower band predominantly expressed in sSEPSIS samples. FIG. 5C: Isoelectric focusing of AAT to demonstrate increased AAT fragmentation in sSEPSIS samples compared to samples from SIRS-PCT+ patients. FIG. 5D: To substantiate that the 4.79 kDa peak is generated by cleavage of AAT in sSEPSIS patients we incubated AAT with a small amount of plasma from sSEPSIS patients; AAT is cleaved in the presence of sSEPSIS plasma resulting in a 4.78 kDa fragment. FIG. 5E: Representative ProteinChip Array profile after precipitation of contaminating serum proteins in the presence of reductants. AAT enrichment is demonstrated by an increase in intensity of the AAT peaks at 55.7 kDa and the double labeled peak in the range of 28 kDa (55982.11+2H) compared to an almost absent albumin peak.

FIG. 6: Amino acid sequences

Amino acid sequences of the active center of antitrypsin (with sizes).

Figure 7:
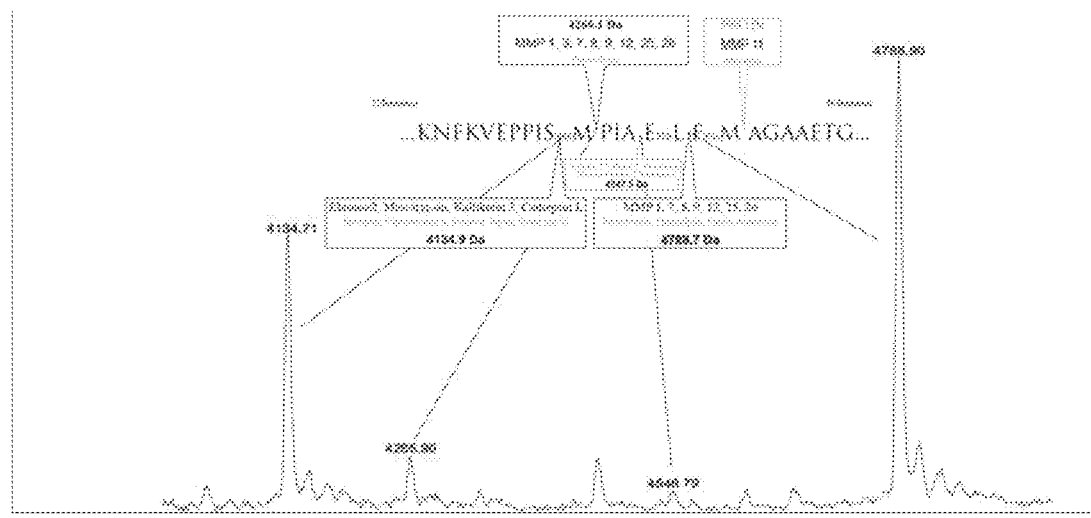

FIG. 7: Sepsis patient

SELDI spectrum from a sepsis patient with antitrypsin fragments.

Figure 8:
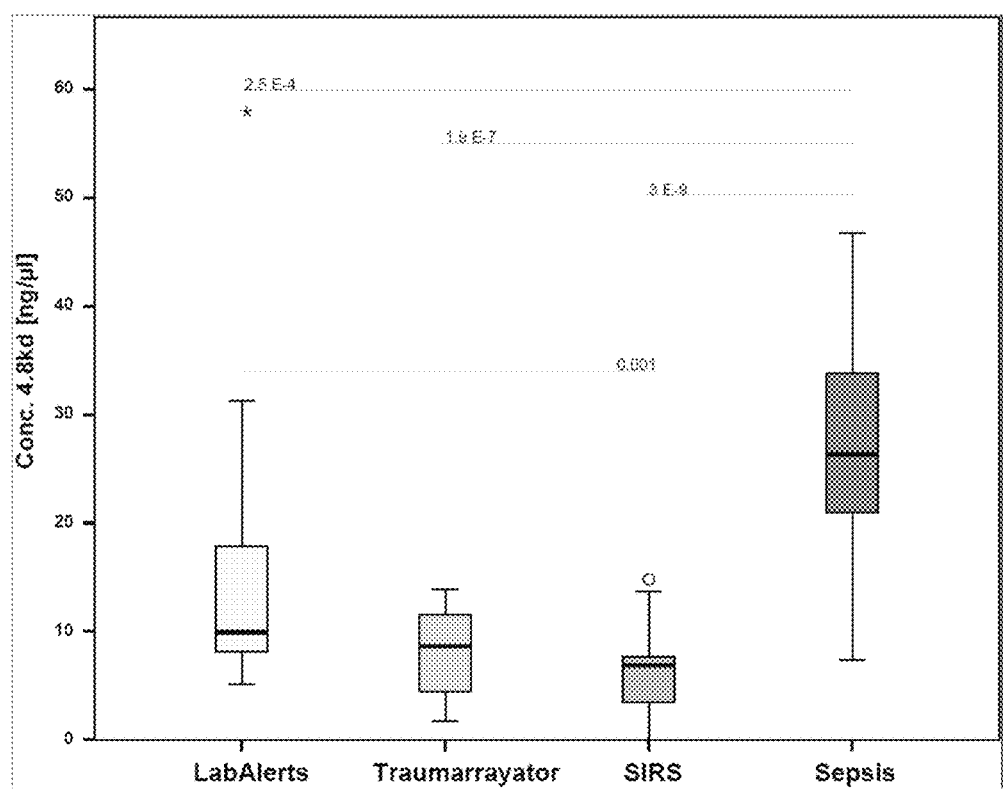

FIG. 8: Sepsis patient

Quantification of the 4.8 kd antitrypsin fragments by means of LC-MS within four patient populations. The levels are significantly higher in patient populations with underlying infection when compared to polytrauma- and SIRS patients without infection. A medium high concentration may be measure in patients with neutropenia and a mild infection.

FIG. 9: α1-antitrypsin complete amino acid sequence (N- to C-terminal) and fragments thereof.

Figure 10:
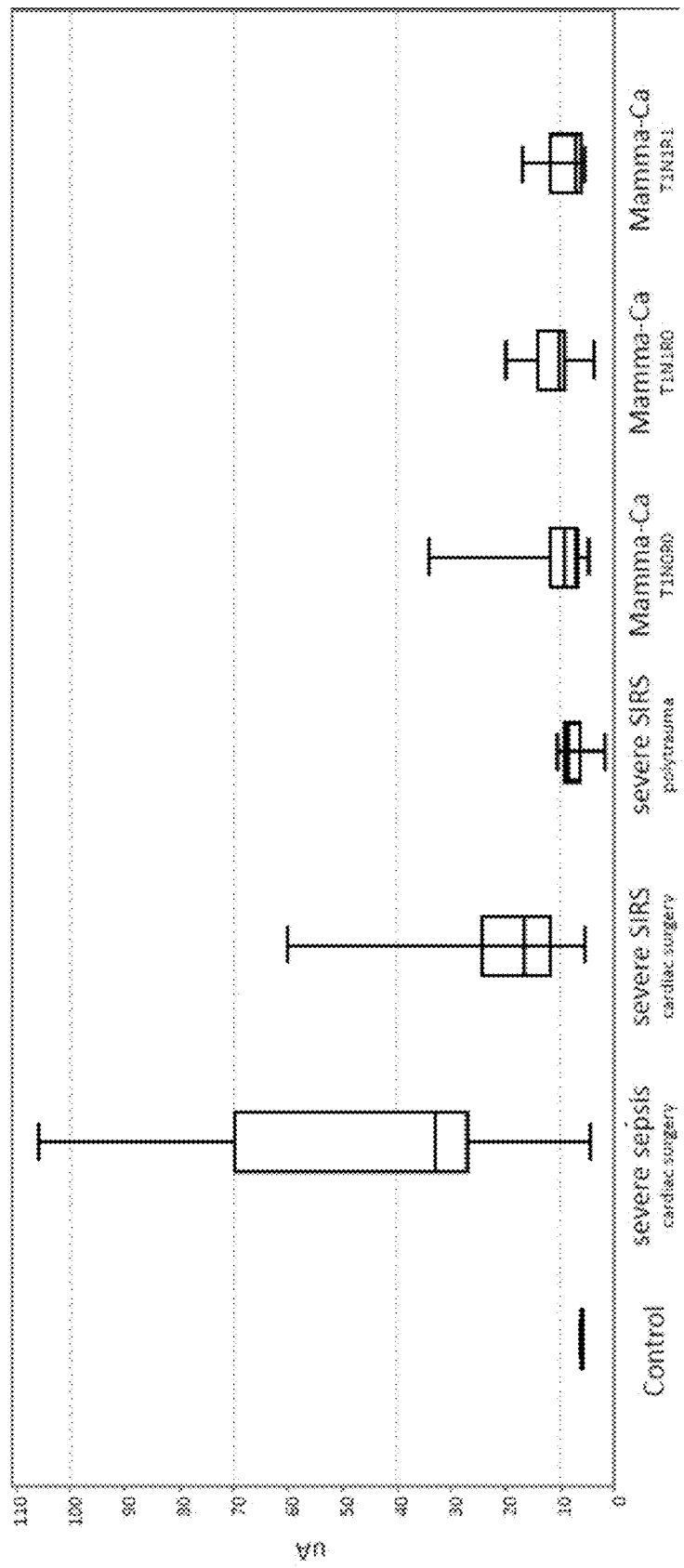

FIG. 10: The biomarker level is only increased in patients with severe sepsis.

Comparison of biomarker level in samples taken from subjects having severe sepsis or severe SIRS with biomarker level in samples taken from subjects having mastocarcinoma (Mamma-Ca).

EXAMPLES

Table 1: Clinical Characteristics of Patients

Data are presented as mean±SD (values were rounded to the tenths place) and percentages. SIRS-PCT-stands for PCT serum levels<0.3 ng/ml; SIRS-PCT+ stands for PCT serum levels>0.3 ng/ml. *APACHE-II=Acute Physiology and Chronic Health Evaluation. This scale ranges from 0 to 71 with higher scores indicating a greater severity of illness. **SOFA=Sequential Organ Failure Assessment Score. Subscores on SOFA range from 0 to 4 for each of six organ systems, with an aggregate score of 0 to 24 and with higher scores indicating more severe organ dysfunction.

Material and Methods

Patients admitted to the surgical intensive care unit (ICU) of the Dept. of Anesthesiology and Intensive Care Medicine from September 2002 until September 2003 and from January 2006 until March 2006 were enrolled in this study if they fulfilled the sepsis criteria according to the ACCP/SCCM consensus conference or the criteria for SIRS of non-infectious origin with acute organ dysfunction, respectively (ICD-10-GM code).

In patients with SIRS of non-infectious origin blood samples were obtained after admission to the ICU; in 67 SIRS patients (83%) within 24 hours, in 7 patients (8.6%) within 48 hours and for the remaining patients in more than 48 hours after ICU admission and in patients with severe sepsis/septic shock within 24 hours after onset of the first sepsis-induced organ dysfunction. Patients less than 18 years old, pregnant, or lacking informed consent were excluded. Patients with SIRS of non-infectious origin were further stratified by their procalcitonin serum concentrations on the day of enrollment. PCT serum levels<0.3 ng/ml were classified as PCT-negative SIRS (SIRS-PCT−), elevated PCT serum levels were classified as PCT-positive SIRS (SIRS-PCT+). The local ethics committee approved this study.

According to a standardized protocol; 10 ml arterial blood was drawn into EDTA tubes (Sarstedt, Nuembrecht, Germany); immediately followed by adding 800 µl of a protease inhibitor cocktail (Complete Mini, Roche Diagnostics GmbH, Mannheim, Germany). Tubes were gently mixed and centrifuged at 3750 rpm (2516 g at the middle of the tube) at 4° C. for 10 minutes; plasma aliquots were immediately frozen at −80° C. In total 166 samples from 159 individual patients were collected; in 7 patients who changed their status e.g. from SIRS to sSEPSIS two samples were collected at different time points during ICU stay and allocated to the respective sample groups.

SELDI-TOF mass spectrometry was conducted on a Series 4000 ProteinChip SELDI reader (Bio-Rad, Hercules, Calif.); a Biomek 2000 liquid-handling station was used for sample dilution and processing of ProteinChips. Samples were thawed over night at 4° C. and analyzed in duplicates. Aliquots were thawed once or twice, for the third and first experiment, respectively. In the second experiment, remaining aliquots from the first experiment, already denatured with U9 buffer and then stored at −80° C. until analysis, were used. For protein chip analysis, 40 µl samples were denatured with 60 µl denaturing buffer (9M Urea, 1% Chaps) and incubated for 30 minutes. 20 µl of the denatured sample were diluted 1 to 5 in 0.1 mol/L Tris-HCl, pH 9.0 (Q10), or 0.05 mol/L HEPES pH 7.3 (CM10) and loaded on Q10 ProteinChip Arrays (strong anion exchange array; Ciphergen Biosystems Inc, Fremont, Calif.) and CM10 ProteinChip Arrays (weak cation exchange array; Ciphergen Biosystems Inc, Fremont, Calif.) respectively, after appropriate chip pre-treatment and washing. After 30 minutes of incubation at room temperature on a DPC MicroMix 5 shaker (Promega, Madison, Wis.) chips were washed three times with appropriate buffers and rinsed two times with water. To remove remaining liquid ProteinChips were centrifuged for 10 seconds at 2950 rpm and air dried for 5 minutes. 1 µl of a saturated energy-absorbing molecule (EAM) solution (5 mg sinapinic acid dissolved in 75 µl acetonitrile and 75 µl 1% trifluoroacetic acid) were applied to the spot surface before chips were analyzed. Mass analysis was performed in a ProteinChip Reader (PCS 4000, Ciphergen Biosystems Inc, Fremont, Calif.) with an automated data collection protocol including 350 laser shots. A 1-200 kDa mass range, divided into two spectral parts: 1-30 kDa and 30-200 kDa, was used. Laser energy was set to 3000 nj and 4900 nj for CM10 chips (warming shots 3700 nj and 5500 nj) and 3250 nj and 5200 nj for Q10 chips (warming shots 3750 nj and 5900 nj) for the 1-30 kDa and 30-200 kDa measurements, respectively. For each point, the data were averaged to a spectrum. Mass accuracy was calibrated internally with known protein standards and externally using all-in-one peptide/protein molecular weight standard.

Spectra were normalized by total ion current (TIC). In most cases, specifically for the first decision trees, this was done in two different regions (1.5-200 kDa and 5.5-200 kDa); spectra with normalization factors above 2.55 and below 0.42 times the mean normalization factor were excluded from the analysis. To ensure comparability of peak intensities between different experiments external normalization coefficients, which had been obtained after normalization of the first experiment, were used. Peaks detected using Ciphergen Express Software (Version 3.0; Ciphergen Biosystems Inc, Fremont Calif.) in three different regions (i.e., m/z 1500-10000, 10000-30000, 30000-200000) for each chip type. Peak Clusters were detected after baseline subtraction under the following conditions: S/N-ratio>5 with a minimum peak threshold of 5% for the first pass and a S/N-ratio>2 with a cluster mass window of 0.1%-0.3% depending on the cluster region analyzed for cluster completion in the second pass. Intensity values for each peak were then averaged for each duplicate sample pair analyzed. Peak data for the three different m/z regions were exported as CSV files into Microsoft Excel (Microsoft, Redmond, Wash.). CART analysis was performed using Ciphergen Biomarker Pattern software (BPS) version 5.0. CSV files containing peak data of the three different mass regions from the two chip types were merged to obtain one file comprising the peak intensities of the entire mass range (1.5-200 kDa). Data from the training set were imported into the BPS and a classification tree was set up as previously described.

Statistical analysis was performed using SPSS 18. For calculation of mean peak intensities and creation of boxplots and ROC curves of individual markers of the second decision tree (FIG. S2 A-C) only samples with complete datasets for all three markers were included.

Proteins where purified by anion exchange chromatography and/or one-dimensional SDS-PAGE. Spots with a corresponding size were excised; trypsin digested in-gel and subjected to MS analysis. For details see supplemental text in the data supplement that accompanies the online version of this article.

α-1 Antitrypsin (AAT) was enriched according to a modified method from Glaser et al. (15). Transthyretin (TTR) was measured by rate nephelometry on an IMMAGE® Immunochemistry System according to the manufacturer's instructions (Beckman Coulter, Brea, Calif.).

Results

To test the ability of SELDI-TOF MS to distinguish patients with non-infectious caused SIRS from patients with sSEPSIS, plasma protein profiles were analyzed in samples from patients grouped according to clinical ACCP/SCCM consensus criteria. 166 samples from 159 individual patients, 81 samples from patients with severe sepsis or septic shock (sSEPSIS) and 85 samples from patients with SIRS without infection were enrolled. In 7 patients who changed their status e.g. from SIRS to sSEPSIS two samples were included and allocated to their respective sample groups. Patients with SIRS of non-infectious origin were further classified according to their PCT serum concentrations on the day of enrollment in PCT-negative (PCT<0.3 ng/ml) SIRS patients (SIRS-PCT−) and PCT-positive (PCT>0.3 ng/ml) SIRS patients (SIRS-PCT+).

The protocol for identifying diagnostic mass patterns included the following steps: (1) Analysis of a training set comprising samples with known diagnosis, to obtain a decision tree; (2) validation of the discriminative power of a given decision tree in a test set from additional patients in the same cohort; (3) a test for reproducibility of this discrimination by repeating the analysis of the same test set at 5 months later; and (4) replication of the analysis on an independent, blinded test set. The clinical characteristics of SIRS-PCT−, SIRS-PCT+ and sSEPSIS patients assigned to the training, test and prospective test group are depicted in Table 1.

A Refined Algorithm Distinguishes SIRS-PCT-Positive and sSepsis Patients but is Dependent on Aprotinin Related to Trasylol Therapy PCT Fails to Discriminate SIRS from sSEPSIS Patient Samples We first evaluated the diagnostic value of PCT for discrimination of patients with infectious and non-infectious induced SIRS in our study cohort. Median values of PCT for the SIRS (n=75; PCT=6.79 [median]; 3.38-11.50 [25-75 percentile]) and sSEPSIS samples (n=72; PCT=4.02 [median]; 1.84-12.46 [25-75 percentile]) were not significant different (p=0.62 Mann Whitney U test). ROC curve analysis revealed that PCT is insufficient for discrimination of SIRS from sSEPSIS patient samples (AUC=0.525; 95% CI=0.428-0.621; online Supplemental FIG. S1A). This holds true if we look at discriminatory power of PCT to distinguish only SIRS-PCT+ from sSEPSIS samples in the training, test and prospective test group (AUC=0.411-0.69; online Supplemental FIG. S1B-D).

An Algorithm Discriminates SIRS-PCT+ Patients from sSEPSIS Patients and is Validated in a Blinded Test Set Next we asked the question whether mass profiling could further stratify SIRS-PCT+ from sSEPSIS patients. To this end CART analysis was performed with spectra from 54 patients (sSEPSIS:n=31, PCT=25.84±75.4; SIRS-PCT+: n=23 PCT=20.01±34.3; Table 1). Classification algorithms obtained revealed a peak at 6.5 kDa as important for discrimination of sSEPSIS and SIRS-PCT+ cases. Two example algorithms depicted in FIG. 1 allowed correct identification of 96% and 100% of sSEPSIS and SIRS-PCT+ cases, respectively. For validation of these results a blinded test set comprising 77 additional patients (Table 1) from the same series (SIRS-PCT+:n=36, PCT=16.98±26.1; sSEPSIS: n=41, PCT=15.82±33.1) was used. Again, the classification algorithms depicted in FIG. 1A/B correctly predicted 37/36 patients with sSEPSIS and 24/25 SIRS-PCT+ patients, respectively (sensitivity=90.2%/87.8%, specificity=66.6%/69.4% (AUC for prediction of the test set: sSEPSIS=0.756/0.753).

Replication Shows Reproducibility of the Diagnostic Protein Pattern Analysis Over Time and Allows Clinical Validation in an Independent Test Set The blinded test set was reanalyzed 5 months later using the same conditions as in the training set. Using the same decision trees, we obtained similar results for the correct identification of sSEPSIS (78%; 29/37; AUC=0.841) and SIRS-PCT+ (92.8%; 26/28; AUC=0.872) patients (FIG. 1). For further validation, the analysis was replicated in an independent blinded sample of 19 ICU patients, PCT-positive at the time of sampling and later retrospectively assigned to either the sSEPSIS (n=9) or SIRS-PCT+ (n=10) group according to conventional clinical criteria. As shown in FIG. 1, samples were identified correctly in 77%/66% and 100%/100% of sSEPSIS and SIRS-PCT+ cases, respectively.

CM_6.51 is Identified as Aprotinin Related to Trasylol® Therapy

Next we tried to identify the first differentially expressed marker CM_6.51. In 2002/2003 when samples were collected for this study, patients undergoing coronary artery bypass grafting surgery (CABG) commonly receive aprotinin (Trasylol®) to reduce perioperative blood loss and the need for blood transfusion; most of our SIRS-PCT+ patients underwent cardiac surgery (Table 1). In 70 of 98 cardiac surgery patients records were available for retrospective assessment of aprotinin dosage; most (94.29%) received total Trasylol doses from 0.5 up to 8 million KIU. Aprotinin is a natural proteinase inhibitor with a molecular weight of 6.512 kDa. Evidence that CM_6.51 is aprotinin was provided by comparison of SELDI-TOF spectra after application of Trasylol® on CM10 chips with spectra from SIRS-PCT+ patients who received Trasylol® (FIG. 1). Marker CM_6.51, at 6512.74 Da, corresponds to the aprotinin Peak at 6512.78 Da; furthermore, CM_6.51 is only present in the SIRS-PCT+ patient (sample 162; 5 million KIU Trasylol®) but nearly absent in the sSEPSIS patient (sample 140) who did not receive Trasylol®. CM_6.51 peak intensity correlates with total dose of Trasylol® applied in SIRS patients receiving more than 1.5 million KIU Trasylol® (Pearson correlation coefficient=0.848; p<0.001). CM_6.51, thus, does truly discriminate different patient groups as it reflects prophylactic Trasylol® administration in those patients undergoing cardiopulmonary bypass; yet, it is not a pathophysiological marker in the course of infectious SIRS (severe sepsis/septic shock)/non-infectious SIRS with severe organ dysfunction.

An Alternative Discriminatory Decision Tree is Independent of CM_6.51

For generation of alternative decision trees, we evaluated different analysis settings, e.g. exclusion of the above mentioned marker CM_6.51. FIG. 2 depicts a second decision tree, discriminating sSEPSIS from SIRS-PCT+ patients (93% sensitivity, 95% specificity) in the learning set. Interestingly, this tree comprised two clusters (4.7 kDa, 13.8 kDa) already shown to be important predictors in the first decision trees. The additional main splitter was detected on the Q10 surface with a molecular mass of approximately 55.7 kDa. A representative example of obtained normalized ProteinChip array profiles is shown in FIG. 3. The first validation of this decision tree in the test set resulted in sensitivities and specificities of 85.3% and 86.1% (FIG. 2). This validation was reproduced after 5 months as 86.4% and 92.8% respectively (FIG. 2). Using this decision tree in the independent blinded replication test set resulted again in correct identification of 88.8% and 90% of the patients with sSEPSIS and SIRS-PCT+(Area under the ROC curve (ROC Integral) of the whole classification algorithm AUC=0.911, FIG. 2). Individual ROC areas for the three relevant markers in the first test samples and the independent blinded test samples for prediction of SIRS-PCT+ and sSepsis were in the range of 0.895-0.933 (QC_55.7), 0.656-0.910 (C1_13.8) and 0.712-0.922 (C1_4.7), respectively (online Supplemental FIG. S2 A-C).

Identification of Differentially Expressed Proteins Allows Validation by Conventional Immunoassays and SELDI-TOF MS Immunocapturing For identification of the differentially expressed proteins, samples were used in which the protein peaks of interest were present in high abundance. For identification of the 13.8 kDa protein fraction 4, obtained after fractionation of an aliquot of sample p218 by anion exchange chromatography was purified by a 12% Mini-PAGE. The peak at m/z 55.7 kDa was purified on a 10% Maxi-PAGE; spots with a corresponding size were excised and trypsin digested in-gel. MALDI-TOF/TOF analysis of the obtained fragments and subsequent MASCOT search allowed the identification of marker C1_13.8 as transthyretin (TTR). Assignation of TTR to the differentially expressed 13.8 kDa protein was first confirmed by western blot analysis, showing that TTR is predominately expressed in a SIRS-PCT+ patient while it is not detected in a sSEPSIS patient (FIG. 4A). Second, TTR was measured in 69 sSEPSIS and 59 SIRS-PCT+ samples; mean concentrations were 7.15 mg/dl (95% CI=6.35-7.95) and 10.7 mg/dl (95% CI=10.0-11.5), respectively (FIG. 4B), demonstrating that peak intensities of C1_13.8 correlate with conventional TTR immunoassay results (FIG. S2B). Finally, immune depletion using a TTR specific antibody results in marked reduction of the 13.8 kDa peak intensity compared to the peak intensity observed after using a control antibody (FIG. 4C).

For identification of the peak at m/z 55.7 kDa analysis of three spots obtained after purification on a 10% Maxi-PAGE (FIG. 5A) led to identification of alpha-1-antitrypsin (AAT) and fibrinogen (FBG). Western-blot analysis in SIRS-PCT+ and sSEPSIS patients showed no differences of FBG expression (data not shown); whereas AAT is present in two isoforms with the lower band predominant in sSEPSIS samples (FIG. 5B). This leads us to the assumption that AAT is degraded in patients with sSEPSIS. To confirm this hypothesis we analyzed AAT-isoforms by isoelectric focusing. As shown in FIG. 5C we observed more pronounced AAT fragmentation in the sSEPSIS samples compared to samples from SIRS-PCT+ patients. This result is in agreement with findings from Vissers et al. who has been shown that AAT is cleaved by metalloproteinases released from neutrophils at sites of inflammation (16). The expected fragment is 4790 Da which is exactly the size of the third important discriminatory peak observed in sSEPSIS patients on Q10 Chips at 4.79 kDa. To confirm that this peak is generated by cleavage of AAT in sSEPSIS patients we incubated AAT (Prolastin®, Bayer Vital GmbH, Leverkusen, Germany) with a small amount of plasma from sSEPSIS patients; as shown in FIG. 5D, AAT is cleaved in the presence of sSEPSIS plasma resulting in a 4.78 kDa fragment which is absent in the control sample. This result fits in with the finding that reduced expression of the 55.7 kDa peak observed in sSEPSIS samples (online Supplement FIG. S2C) is accompanied by increased peak intensity in the 50 kDa range (data not shown). Finally, to further confirm that the 55.7 kDa peak corresponds to AAT, we first immunocaptured AAT. Observing only a small reduction in peak intensity for the 55.7 kDa and the double labeled 28 kDa-Peak (data not shown), we then, secondly, enriched AAT based on a modified method from Glaser et al. (15) by precipitation of contaminating plasma proteins in the presence of reductants. As shown in FIG. 5E enrichment of AAT is paralleled by a marked increase of the 55.7 kDa and the double labeled peak in the range of 28 kDa compared to peak intensities of other proteins e.g. albumin, supporting further that the 55.7 kDa peak is indeed AAT.

The invention claimed is:

1. A method of treating a human subject that has or is suspected to have sepsis, the method comprising identifying the human subject with sepsis or an increased risk of sepsis by:

(a) detecting the level of antitrypsin (ATT) or fragments thereof in a sample taken from said human subject using surface enhanced laser desorption ionization-time of flight-mass spectrometry (SELDI-TOF MS), immunoassays or a combination thereof, wherein the ATT fragments are selected from the group consisting of SEQ ID NOs: 2, 3, 4, 5, 6, 7, 8, 9, 10, 11, 12, 13, and 14 or a combination thereof, and wherein said sample is a plasma sample, a serum sample, a whole blood sample, a blood sample or fractions thereof, a lymphatic fluid sample, a urine sample or an extract of any of the aforementioned samples;

(b) correlating the level of ATT or fragments thereof with having sepsis or an increased risk of sepsis and, wherein said having sepsis or increased risk of sepsis is identified if the level of ATT is below a certain cut-off value and/or the level of fragments thereof is above a certain cut-off value;

(c) detecting the level of transthyretin (TTR) using SELDI-TOF MS, immunoassays or a combination thereof the sample taken from said human subject, (d) correlating the level of TTR with sepsis or an increased risk of sepsis and, wherein said sepsis or increased risk of sepsis is identified if the level of TTR is below a certain cut-off value; and (e) administering antimicrobial therapy to the human subject with sepsis or an increased risk of sepsis.

2. The method according to claim 1, wherein steps (b) and/or (d) is are conducted by a method selected from the group consisting of: correlation with respect to the median of the level in an ensemble of predetermined samples, correlation with respect to quantiles in an ensemble of pre-determined samples, and correlation with a mathematical model, such as for example Cox Regression.

3. The method according to claim 1, wherein the cut-off value of the level of ATT of step (b) is about 2 g/l, and may deviate depending on the subject analysed by about 20%; and wherein the cut-off value of the level of TTR of step (d) is about 10 mg/dl, and may deviate depending on the human subject analysed by about 20%.

4. The method according to claim 1, wherein the level of ATT in step (b) is below a median level of a normal population or the level of ATT fragments thereof in step (b) are above a median level of a normal population or the level of TTR in step (d) are below a median of a normal population indicating an increased risk for sepsis in said human subject.

5. The method according to claim 1,
wherein the level of ATT or fragments thereof in step (b) is correlated with a perquantile risk of mortality or survival; and/or the level of TTR in step (d) is correlated with a perquantile risk of mortality or survival.

6. The method according to claim 1, wherein the sample from said human subject is taken at one or more time points: when the subject is first admitted to a medical institution or in an ambulance, when the human subject is in an emergency room, when the human subject is in an intensive care unit, before treatment, after initiation of treatment, 24 hours after initiation of treatment, 48 hours after initiation of treatment and/or 72 hours after initiation of treatment.

7. The method according to claim 1, wherein the level of ATT or fragments thereof in step (b) and/or the level of TTR in step (c) is correlated with an increased risk of sepsis.

* * * * *

SEQUENCE LISTING

```
<160> NUMBER OF SEQ ID NOS: 15

<210> SEQ ID NO 1
<211> LENGTH: 418
<212> TYPE: PRT
<213> ORGANISM: Homo sapiens

<400> SEQUENCE: 1

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
    290                 295                 300
```

```
Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
        355                 360                 365

Thr Glu Ala Ala Gly Ala Met Phe Leu Glu Ala Ile Pro Met Ser Ile
370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys

<210> SEQ ID NO 2
<211> LENGTH: 22
<212> TYPE: PRT
<213> ORGANISM: Homo sapiens

<400> SEQUENCE: 2

Leu Met Ile Glu Gln Asn Thr Lys Ser Pro Leu Phe Met Gly Lys Val
1               5                   10                  15

Val Asn Pro Thr Gln Lys
                20

<210> SEQ ID NO 3
<211> LENGTH: 35
<212> TYPE: PRT
<213> ORGANISM: Homo sapiens

<400> SEQUENCE: 3

Ile Pro Pro Glu Val Lys Phe Asn Lys Pro Phe Val Phe Leu Met Ile
1               5                   10                  15

Glu Gln Asn Thr Lys Ser Pro Leu Phe Met Gly Lys Val Val Asn Pro
            20                  25                  30

Thr Gln Lys
        35

<210> SEQ ID NO 4
<211> LENGTH: 36
<212> TYPE: PRT
<213> ORGANISM: Homo sapiens

<400> SEQUENCE: 4

Ser Ile Pro Pro Glu Val Lys Phe Asn Lys Pro Phe Val Phe Leu Met
1               5                   10                  15

Ile Glu Gln Asn Thr Lys Ser Pro Leu Phe Met Gly Lys Val Val Asn
            20                  25                  30

Pro Thr Gln Lys
        35

<210> SEQ ID NO 5
<211> LENGTH: 37
<212> TYPE: PRT
<213> ORGANISM: Homo sapiens

<400> SEQUENCE: 5
```

```
Met Ser Ile Pro Pro Glu Val Lys Phe Asn Lys Pro Phe Val Phe Leu
1               5                   10                  15
Met Ile Glu Gln Asn Thr Lys Ser Pro Leu Phe Met Gly Lys Val Val
            20                  25                  30
Asn Pro Thr Gln Lys
            35

<210> SEQ ID NO 6
<211> LENGTH: 38
<212> TYPE: PRT
<213> ORGANISM: Homo sapiens

<400> SEQUENCE: 6

Pro Met Ser Ile Pro Pro Glu Val Lys Phe Asn Lys Pro Phe Val Phe
1               5                   10                  15
Leu Met Ile Glu Gln Asn Thr Lys Ser Pro Leu Phe Met Gly Lys Val
            20                  25                  30
Val Asn Pro Thr Gln Lys
            35

<210> SEQ ID NO 7
<211> LENGTH: 39
<212> TYPE: PRT
<213> ORGANISM: Homo sapiens

<400> SEQUENCE: 7

Ile Pro Met Ser Ile Pro Pro Glu Val Lys Phe Asn Lys Pro Phe Val
1               5                   10                  15
Phe Leu Met Ile Glu Gln Asn Thr Lys Ser Pro Leu Phe Met Gly Lys
            20                  25                  30
Val Val Asn Pro Thr Gln Lys
            35

<210> SEQ ID NO 8
<211> LENGTH: 40
<212> TYPE: PRT
<213> ORGANISM: Homo sapiens

<400> SEQUENCE: 8

Ala Ile Pro Met Ser Ile Pro Pro Glu Val Lys Phe Asn Lys Pro Phe
1               5                   10                  15
Val Phe Leu Met Ile Glu Gln Asn Thr Lys Ser Pro Leu Phe Met Gly
            20                  25                  30
Lys Val Val Asn Pro Thr Gln Lys
            35                  40

<210> SEQ ID NO 9
<211> LENGTH: 41
<212> TYPE: PRT
<213> ORGANISM: Homo sapiens

<400> SEQUENCE: 9

Glu Ala Ile Pro Met Ser Ile Pro Pro Glu Val Lys Phe Asn Lys Pro
1               5                   10                  15
Phe Val Phe Leu Met Ile Glu Gln Asn Thr Lys Ser Pro Leu Phe Met
            20                  25                  30
Gly Lys Val Val Asn Pro Thr Gln Lys
            35                  40
```

```
<210> SEQ ID NO 10
<211> LENGTH: 42
<212> TYPE: PRT
<213> ORGANISM: Homo sapiens

<400> SEQUENCE: 10

Leu Glu Ala Ile Pro Met Ser Ile Pro Pro Glu Val Lys Phe Asn Lys
1               5                   10                  15

Pro Phe Val Phe Leu Met Ile Glu Gln Asn Thr Lys Ser Pro Leu Phe
            20                  25                  30

Met Gly Lys Val Val Asn Pro Thr Gln Lys
        35                  40

<210> SEQ ID NO 11
<211> LENGTH: 43
<212> TYPE: PRT
<213> ORGANISM: Homo sapiens

<400> SEQUENCE: 11

Phe Leu Glu Ala Ile Pro Met Ser Ile Pro Pro Glu Val Lys Phe Asn
1               5                   10                  15

Lys Pro Phe Val Phe Leu Met Ile Glu Gln Asn Thr Lys Ser Pro Leu
            20                  25                  30

Phe Met Gly Lys Val Val Asn Pro Thr Gln Lys
        35                  40

<210> SEQ ID NO 12
<211> LENGTH: 44
<212> TYPE: PRT
<213> ORGANISM: Homo sapiens

<400> SEQUENCE: 12

Met Phe Leu Glu Ala Ile Pro Met Ser Ile Pro Pro Glu Val Lys Phe
1               5                   10                  15

Asn Lys Pro Phe Val Phe Leu Met Ile Glu Gln Asn Thr Lys Ser Pro
            20                  25                  30

Leu Phe Met Gly Lys Val Val Asn Pro Thr Gln Lys
        35                  40

<210> SEQ ID NO 13
<211> LENGTH: 45
<212> TYPE: PRT
<213> ORGANISM: Homo sapiens

<400> SEQUENCE: 13

Ala Met Phe Leu Glu Ala Ile Pro Met Ser Ile Pro Pro Glu Val Lys
1               5                   10                  15

Phe Asn Lys Pro Phe Val Phe Leu Met Ile Glu Gln Asn Thr Lys Ser
            20                  25                  30

Pro Leu Phe Met Gly Lys Val Val Asn Pro Thr Gln Lys
        35                  40                  45

<210> SEQ ID NO 14
<211> LENGTH: 394
<212> TYPE: PRT
<213> ORGANISM: Homo sapiens

<400> SEQUENCE: 14

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
```

```
            20                  25                  30
Phe Ala Phe Ser Leu Tyr Arg Gln Leu Ala His Gln Ser Asn Ser Thr
            35                  40                  45

Asn Ile Phe Phe Ser Pro Val Ser Ile Ala Thr Ala Phe Ala Met Leu
        50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
        355                 360                 365

Pro Phe Val Phe Leu Met Ile Glu Gln Asn Thr Lys Ser Pro Leu Phe
    370                 375                 380

Met Gly Lys Val Val Asn Pro Thr Gln Lys
385                 390

<210> SEQ ID NO 15
<211> LENGTH: 376
<212> TYPE: PRT
<213> ORGANISM: Homo sapiens

<400> SEQUENCE: 15
```

-continued

```
Met Pro Ser Ser Val Ser Trp Gly Ile Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
            35                  40                  45

Lys Ile Thr Pro Asn Leu Ala Glu Phe Ala Phe Ser Leu Tyr Arg Gln
50                      55                  60

Leu Ala His Gln Ser Asn Ser Thr Asn Ile Phe Phe Ser Pro Val Ser
65                      70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
            115                 120                 125

Gln Pro Asp Ser Gln Leu Gln Leu Thr Thr Gly Asn Gly Leu Phe Leu
            130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
            195                 200                 205

Val Asn Tyr Ile Phe Phe Lys Gly Lys Trp Glu Arg Pro Phe Glu Val
            210                 215                 220

Lys Asp Thr Glu Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
            275                 280                 285

Asn Glu Leu Thr His Asp Ile Ile Thr Lys Phe Leu Glu Asn Glu Asp
            290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
            355                 360                 365

Thr Glu Ala Ala Gly Ala Met Phe
370                 375
```